(12) United States Patent
Schumacher et al.

(10) Patent No.: US 11,166,754 B2
(45) Date of Patent: Nov. 9, 2021

(54) STRIKE INSTRUMENT FOR INTRAMEDULLARY NAIL

(71) Applicant: DEPUY SYNTHES PRODUCTS, INC., Raynham, MA (US)

(72) Inventors: Yvonne Schumacher, Solothurn (CH); Gaser El Zoghbi, Solothurn (CH); Nicholas Van Stolk, Somerville, NJ (US); Dominik Daniel Bini Falconi, Rothrist (CH)

(73) Assignee: DePuy Synthes Products, Inc., Raynham, MA (US)

(*) Notice: Subject to any disclaimer, the term of this patent is extended or adjusted under 35 U.S.C. 154(b) by 210 days.

(21) Appl. No.: 16/574,983

(22) Filed: Sep. 18, 2019

(65) Prior Publication Data

US 2021/0077161 A1    Mar. 18, 2021

(51) Int. Cl.
*A61B 17/72* (2006.01)
*A61B 17/86* (2006.01)
*A61B 17/92* (2006.01)
*A61B 17/29* (2006.01)

(52) U.S. Cl.
CPC .......... *A61B 17/7266* (2013.01); *A61B 17/86* (2013.01); *A61B 17/921* (2013.01); *A61B 17/725* (2013.01); *A61B 2017/293* (2013.01)

(58) Field of Classification Search
CPC ... A61B 17/7266; A61B 17/86; A61B 17/921; A61B 17/725; A61B 17/72; A61B 17/162; A61B 17/1624; A61B 17/32002; A61B 17/8866; A61B 2017/293; A61B 2017/00473; A61B 2017/00482; A61B 2017/00464; A61B 2017/1602

USPC ........................................................... 606/63
See application file for complete search history.

(56) References Cited

U.S. PATENT DOCUMENTS

| 4,398,322 | A | 8/1983 | Ewen |
| 5,499,985 | A | 3/1996 | Hein et al. |
| 6,126,359 | A | 10/2000 | Dittrich et al. |
| 7,175,633 | B2* | 2/2007 | Roth .................. A61B 17/1725 606/104 |
| 7,549,994 | B2 | 6/2009 | Zander et al. |
| 7,621,921 | B2 | 11/2009 | Parker |

(Continued)

FOREIGN PATENT DOCUMENTS

WO    2011/017066 A1    2/2011

*Primary Examiner* — Pedro Philogene
(74) *Attorney, Agent, or Firm* — Wayne C. Jaeschke, Jr.

(57) ABSTRACT

In one embodiment, a strike instrument that couples to an insertion handle of an intramedullary nail has a shaft that extends along a shaft axis, and an abutment that extends outward relative to the shaft. The abutment is rotationally fixed to the shaft such that the shaft can rotate the abutment between a first orientation, where the abutment can be removed or inserted into the insertion handle, and a second orientation, where the abutment forms an interference with the insertion handle that prevents the abutment from being removed from the handle. The strike instrument includes a strike surface that can transfer an impaction force to the insertion handle, and a lock that engages the insertion handle so as to prevent the abutment from rotating from the second orientation to the first orientation after the abutment is rotated within the insertion handle from the first orientation to the second orientation.

20 Claims, 16 Drawing Sheets

(56) References Cited

U.S. PATENT DOCUMENTS

| | | | |
|---|---|---|---|
| 7,727,240 B1 * | 6/2010 | Benton | A61B 17/1725 606/98 |
| 8,080,015 B2 | 12/2011 | Büttler et al. | |
| 8,361,077 B2 | 1/2013 | Keller | |
| 8,556,976 B2 | 10/2013 | Jacofsky et al. | |
| 9,439,780 B2 | 9/2016 | Witt et al. | |
| 10,335,194 B2 * | 7/2019 | Greenhalgh | A61B 17/3403 |
| 2016/0175112 A1 | 6/2016 | Pruvost et al. | |
| 2018/0353232 A1 | 12/2018 | Barth et al. | |

* cited by examiner

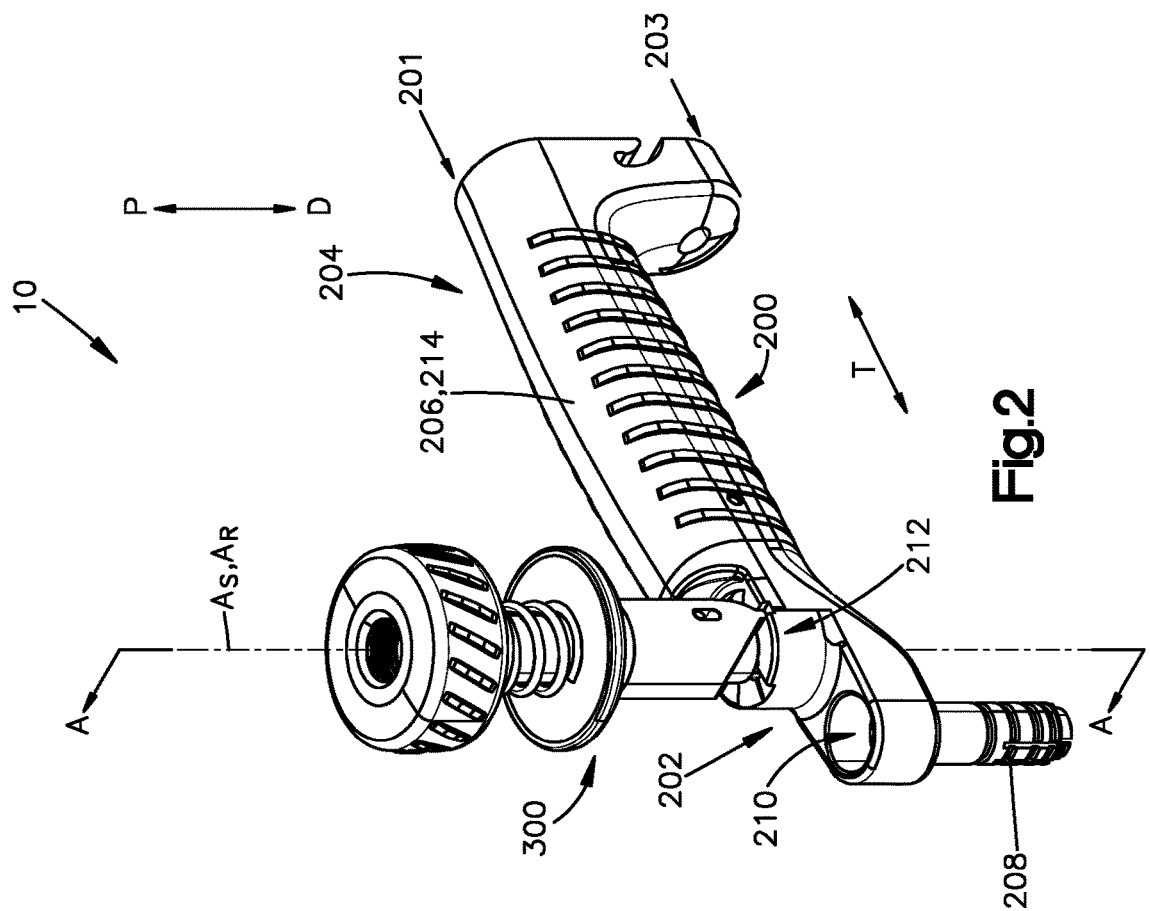
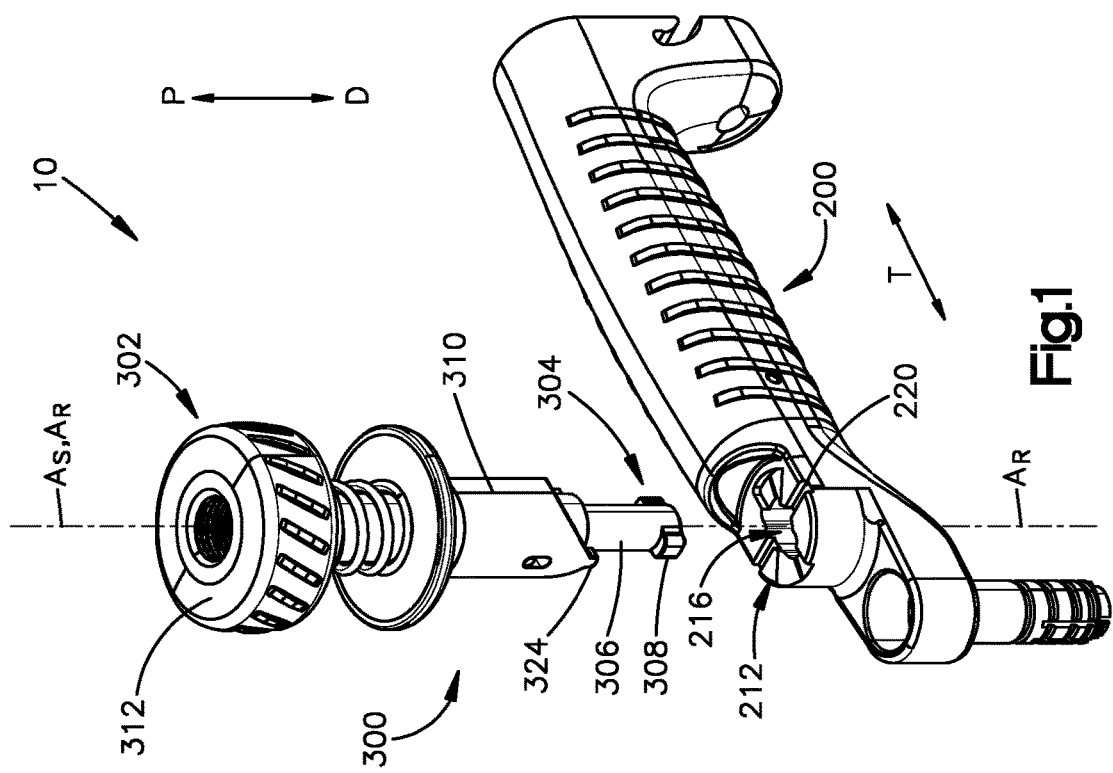

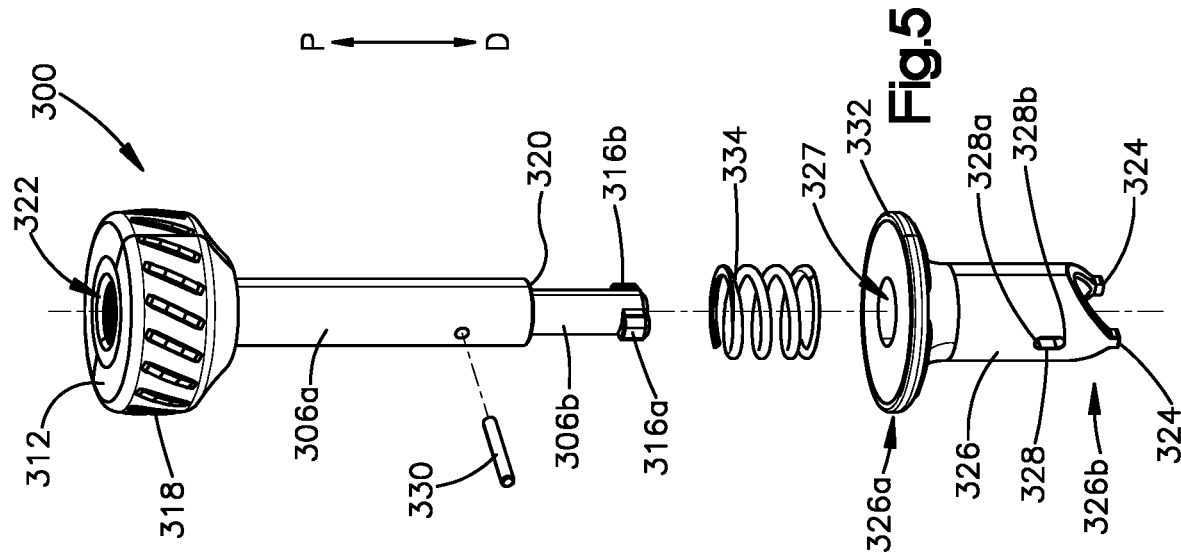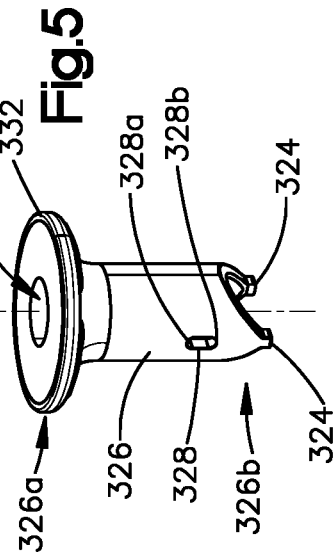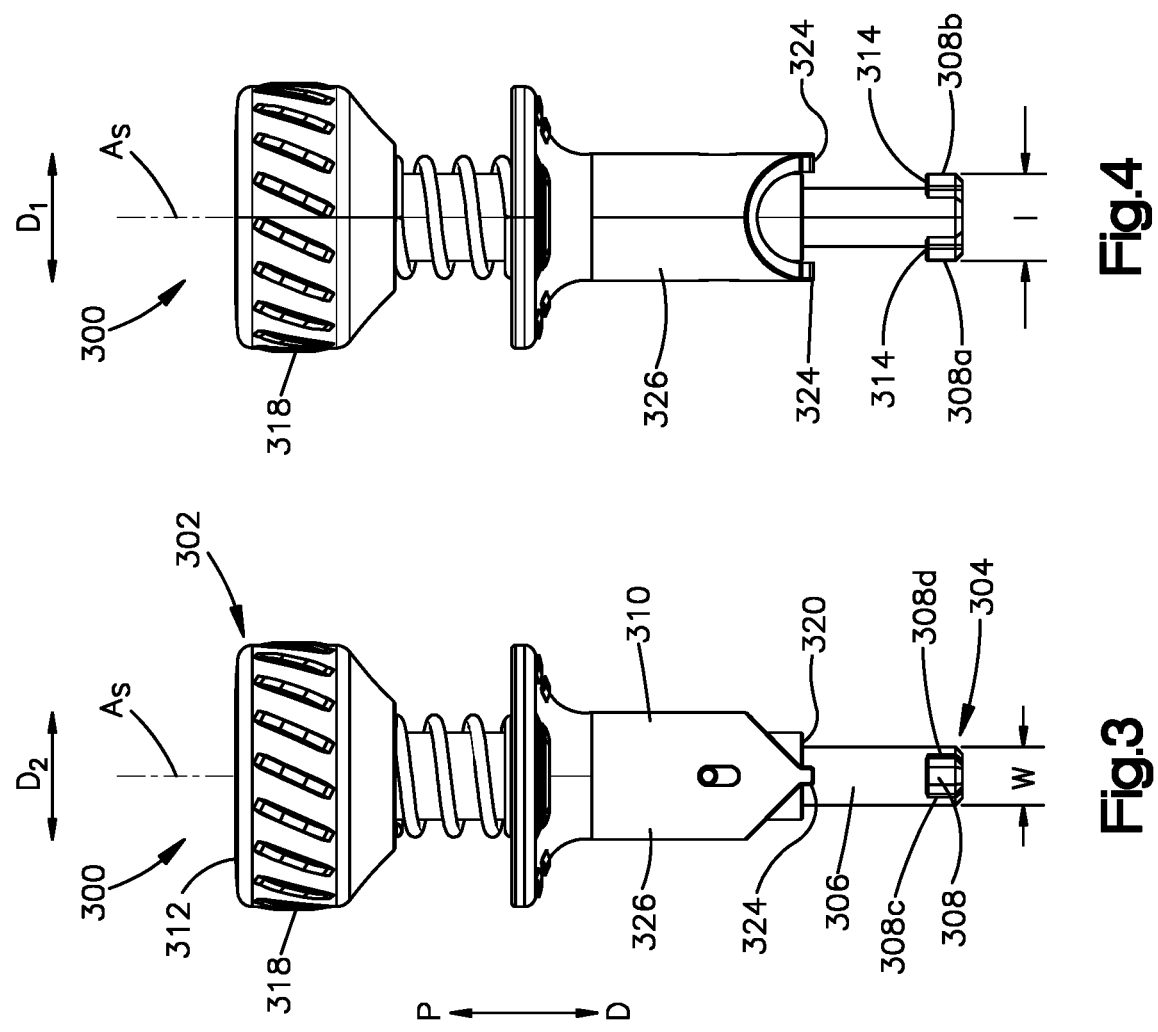

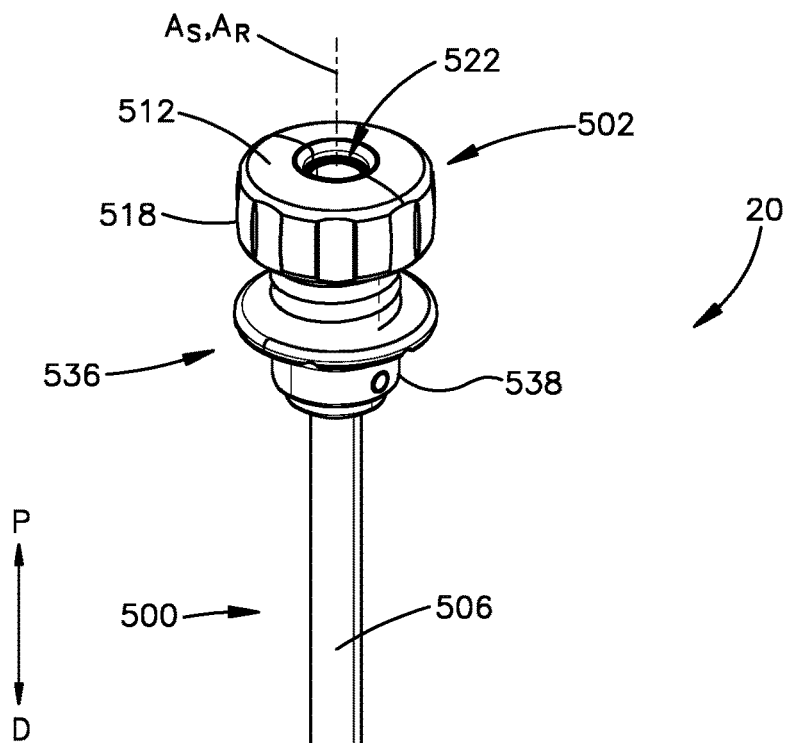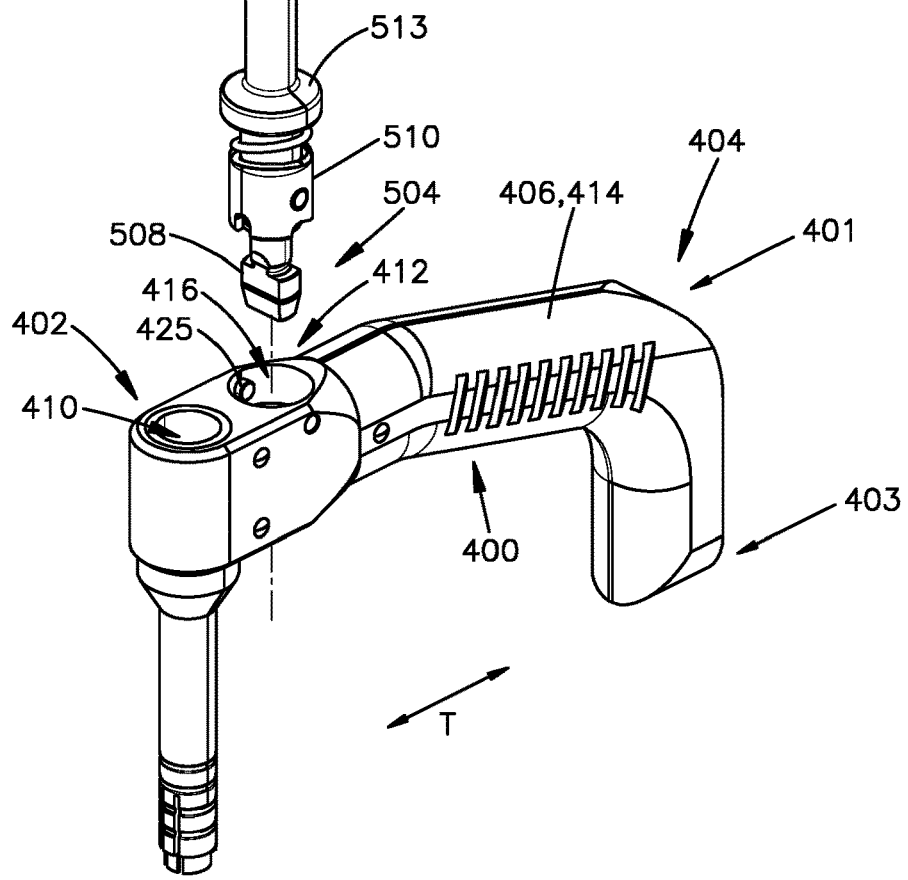
Fig.9

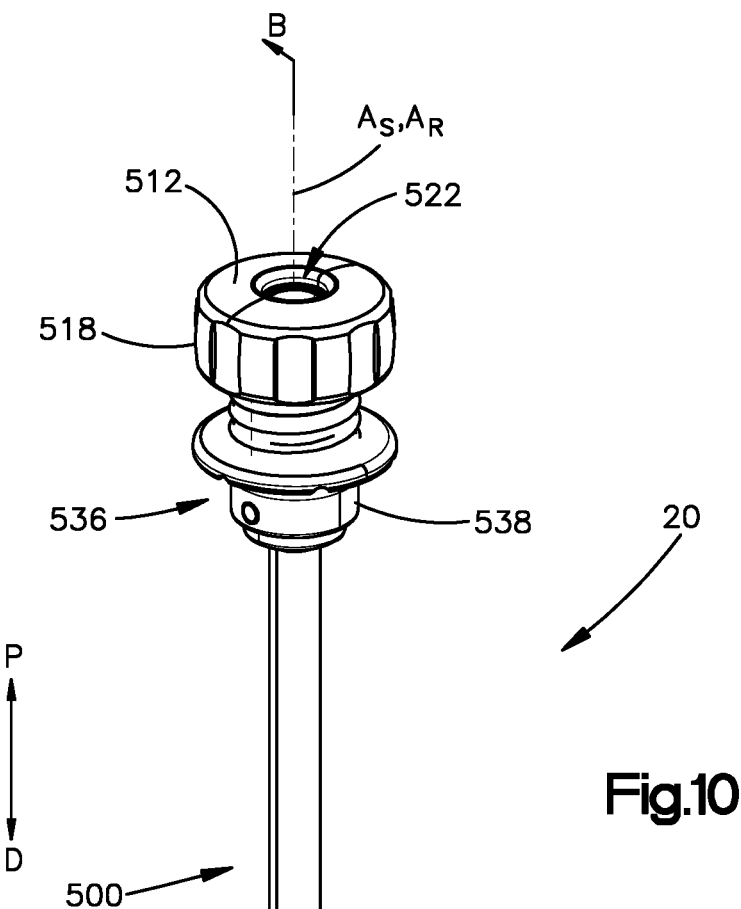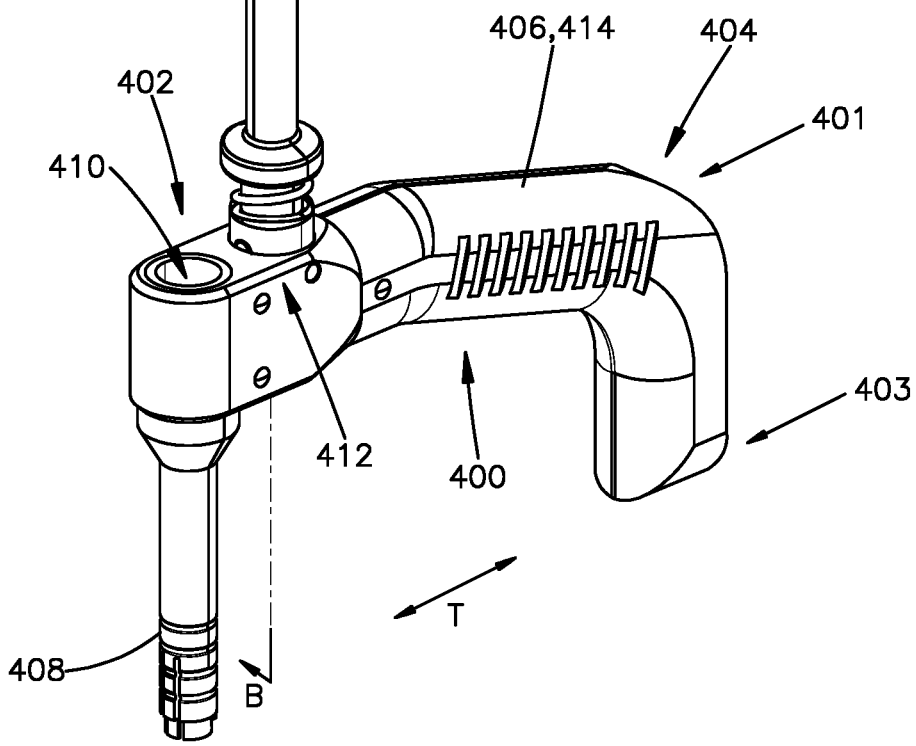

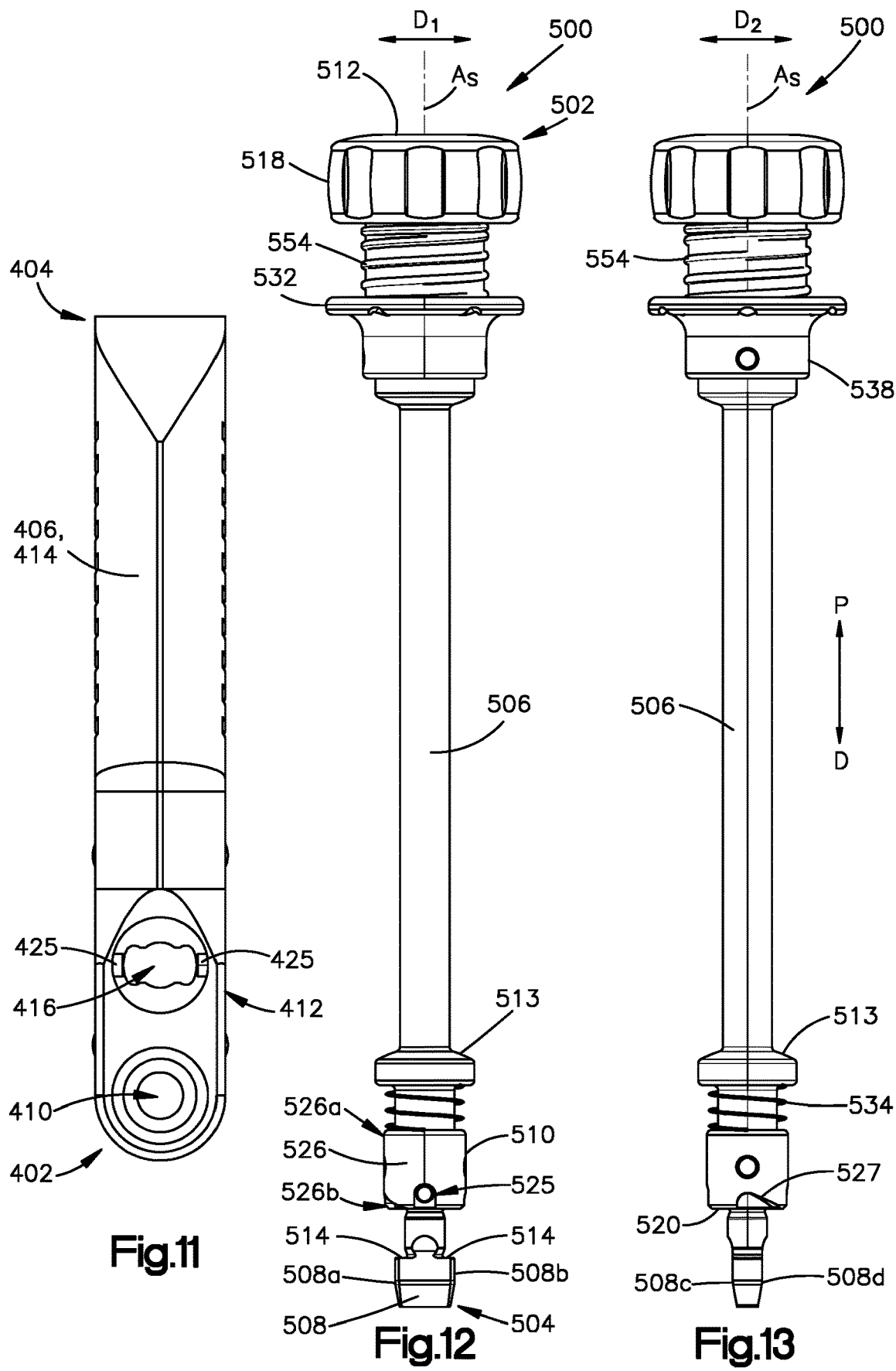

B-B

B-B

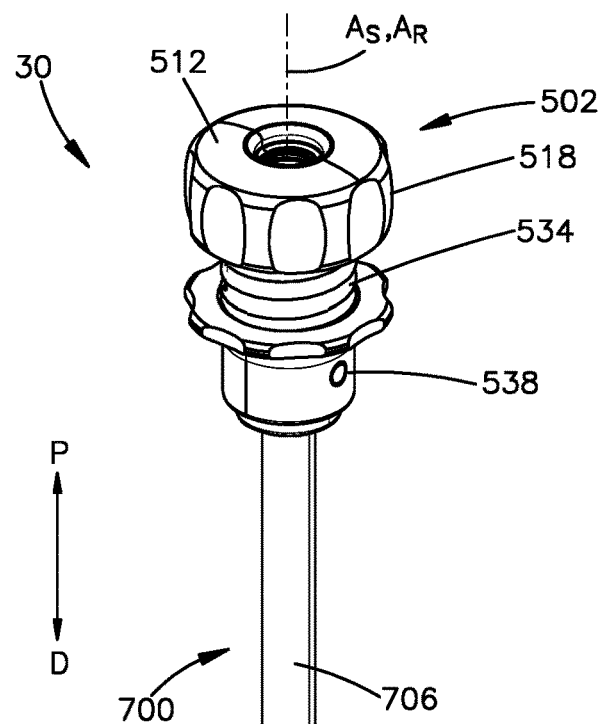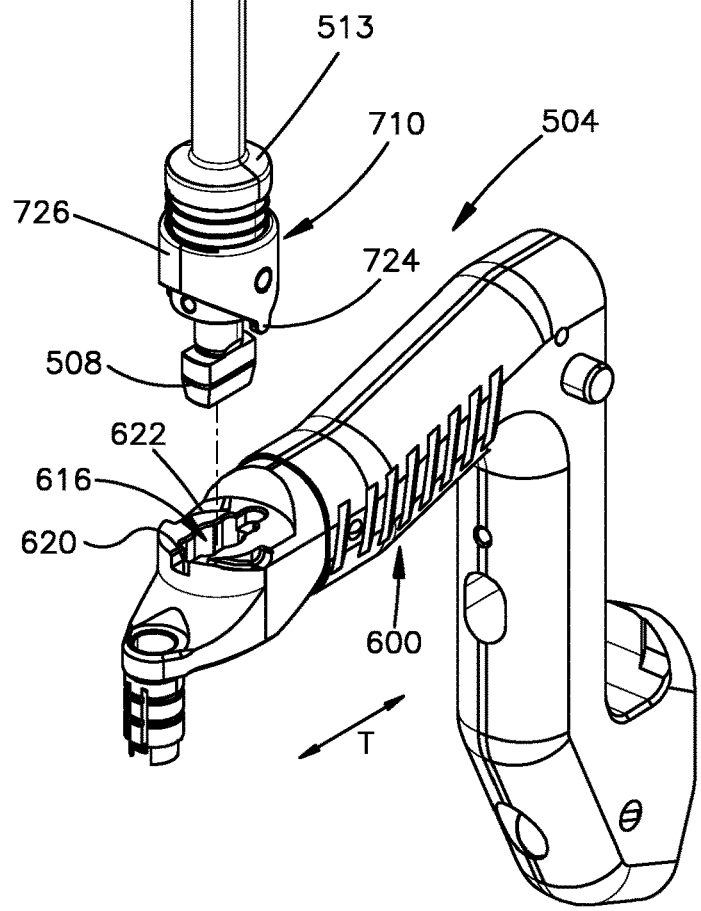
Fig.17

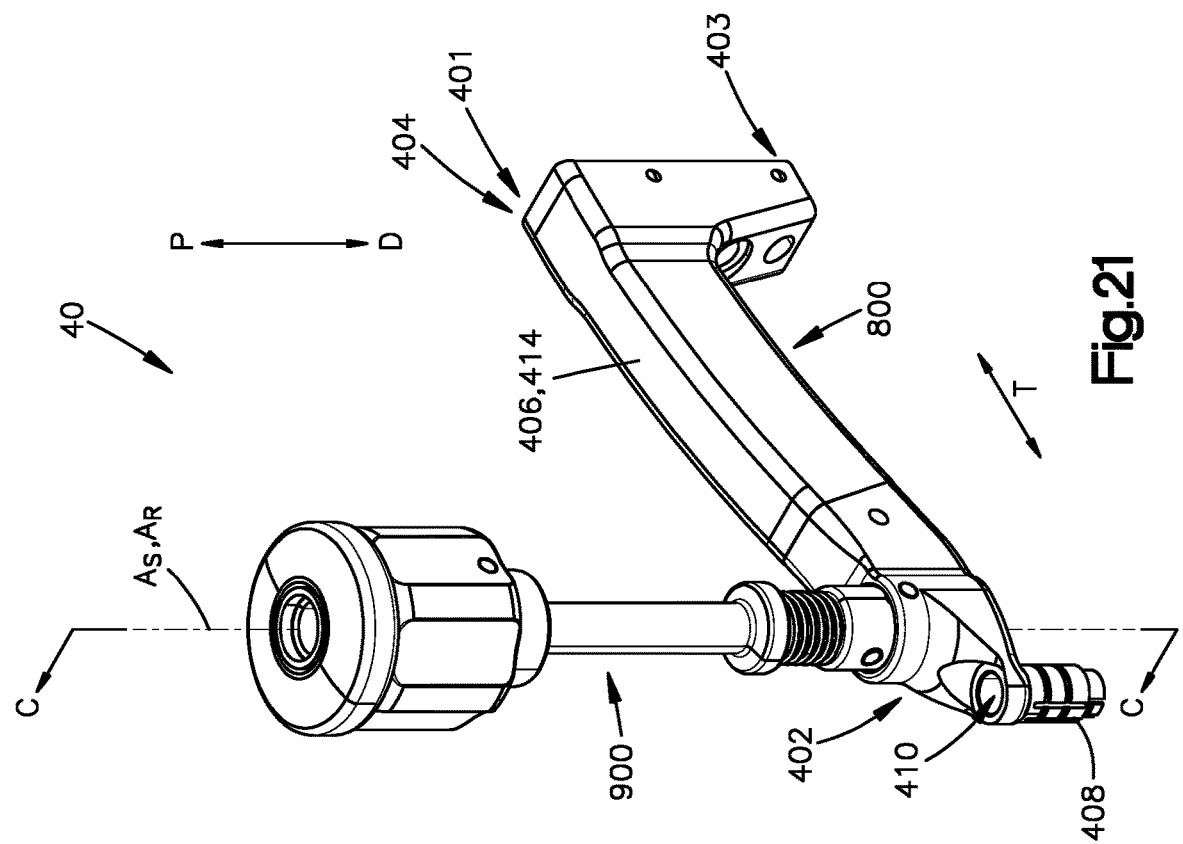
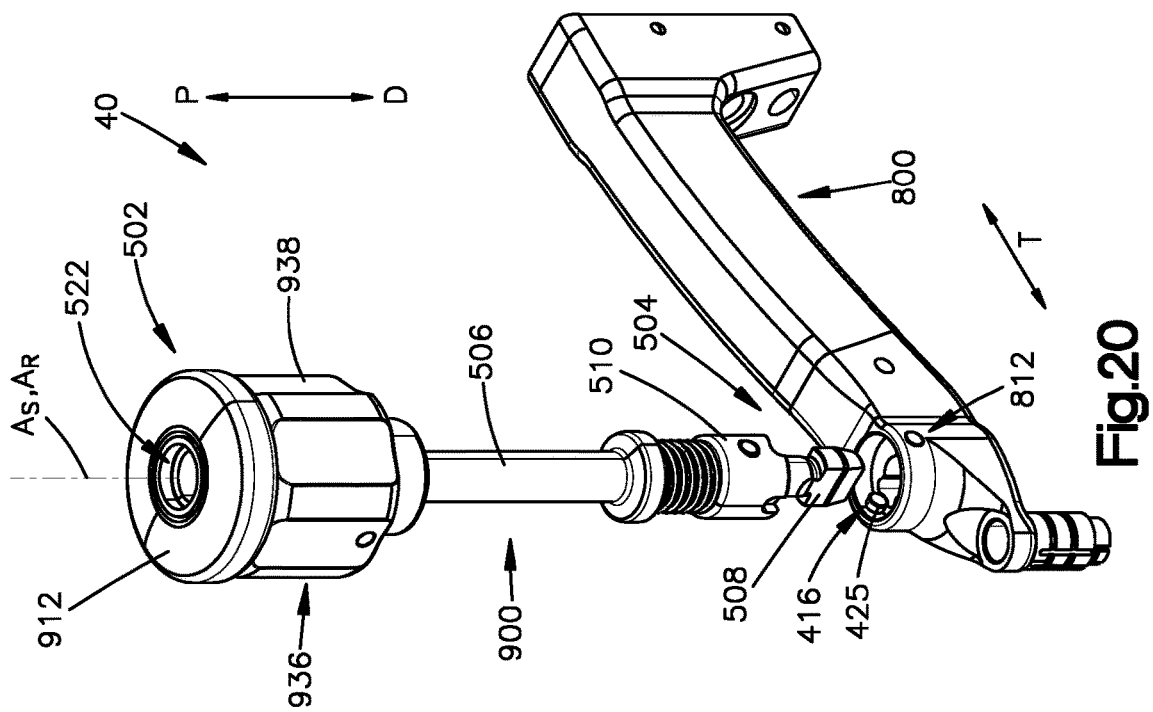

C-C

C-C

STRIKE INSTRUMENT FOR INTRAMEDULLARY NAIL

TECHNICAL FIELD

The present disclosure relates to systems, assemblies, and methods for the insertion and fixation of a nail into an intramedullary canal of a bone.

BACKGROUND

Intramedullary nails have long been used to treat fractures in long bones of the body such as fractures in femurs, tibias, and humeri. To treat such fractures, the intramedullary nail is inserted into a medullary canal of the long bone such that the nail extends spans across one or more fractures in the long bone to fragments of the long bone that are separated by the one or more fractures. Bone anchors are then inserted through the bone and into the intramedullary nail at opposing sides of the fracture, thereby fixing the intramedullary nail to the bone. The intramedullary nail can remain in the medullary canal at least until the fracture is fused.

SUMMARY

In an example embodiment, a strike instrument is configured to couple to an insertion handle of an intramedullary nail. The strike instrument comprises a proximal end, and a distal end that is opposite the proximal end along a distal direction. The strike instrument comprises a shaft that extends between the proximal end and the distal end along a shaft axis. The strike instrument comprises an abutment that extends outward relative to the shaft along a first direction such that the abutment defines a length in the first direction that is greater than a cross-sectional dimension of the shaft in the first direction. The abutment is rotationally fixed to the shaft such that the shaft is configured to rotate the abutment between a first rotational orientation, wherein the abutment can be removed or inserted into the insertion handle, and a second rotational orientation, wherein the abutment is configured to form an interference with the insertion handle that prevents the abutment from being removed from the insertion handle. The strike instrument comprises a strike surface that is translatably fixed to the shaft and configured to receive an impaction force from an impaction tool so as to transfer the impaction force from the strike instrument to the insertion handle when the strike instrument is coupled to the insertion handle. The strike instrument comprises a lock configured such that, when the abutment is received in the insertion handle and rotated relative to the insertion handle from the first rotational orientation to the second rotational orientation, the lock engages the insertion handle so as to prevent the abutment from rotating from the second rotational orientation to the first rotational orientation.

In another example embodiment, an intramedullary nail insertion system comprises a method of coupling a strike instrument to an insertion handle of an intramedullary nail. The method comprises a step of orienting an abutment of the strike instrument in a first rotational orientation so as to align the abutment with a locking hole of the insertion handle. The method comprises a step of moving the strike instrument along a distal direction so as to insert the abutment into the locking hole. The method comprises a step of rotating the abutment from the first rotational orientation to a second rotational orientation so as to cause the abutment to engage an inner surface of the locking hole, thereby preventing the strike instrument from being removed from the insertion handle along a proximal direction, opposite the distal direction. The method comprises a step of locking the strike instrument in the second rotational orientation relative to the insertion handle.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted.

FIG. 1 shows an exploded perspective view of a system according to one embodiment having an insertion handle and a strike instrument, where the strike instrument is spaced from the insertion handle;

FIG. 2 shows an assembled perspective view of the system of FIG. 1, where the strike instrument is coupled to the insertion handle;

FIG. 3 shows a side elevation view of the strike instrument of FIGS. 1 and 2 according to one embodiment;

FIG. 4 shows a front elevation view of the strike instrument of FIG. 3;

FIG. 5 shows an exploded perspective view of the strike instrument of FIG. 4;

FIG. 9 shows an exploded perspective view of a system according to another embodiment having an insertion handle and a strike instrument, where the strike instrument is spaced from the insertion handle;

FIG. 10 shows an assembled perspective view of the system of FIG. 9, where the strike instrument is coupled to the insertion handle;

FIG. 11 shows a top plan view of the insertion handle of FIGS. 9 and 10 according to one embodiment;

FIG. 12 shows a front elevation view of the strike instrument of FIGS. 9 and 10 according to one embodiment;

FIG. 13 shows a side elevation view of the strike instrument of FIG. 12;

FIG. 17 shows an exploded perspective view of a system according to yet another embodiment having an insertion handle and a strike instrument, where the strike instrument is spaced from the insertion handle;

FIG. 20 shows an exploded perspective view of a system according to yet still another embodiment having an insertion handle and a strike instrument, where the strike instrument is spaced from the insertion handle;

FIG. 21 shows an assembled perspective view of the system of FIG. 20, where the strike instrument is coupled to the insertion handle;

DETAILED DESCRIPTION OF ILLUSTRATIVE EMBODIMENTS

Figure 8:
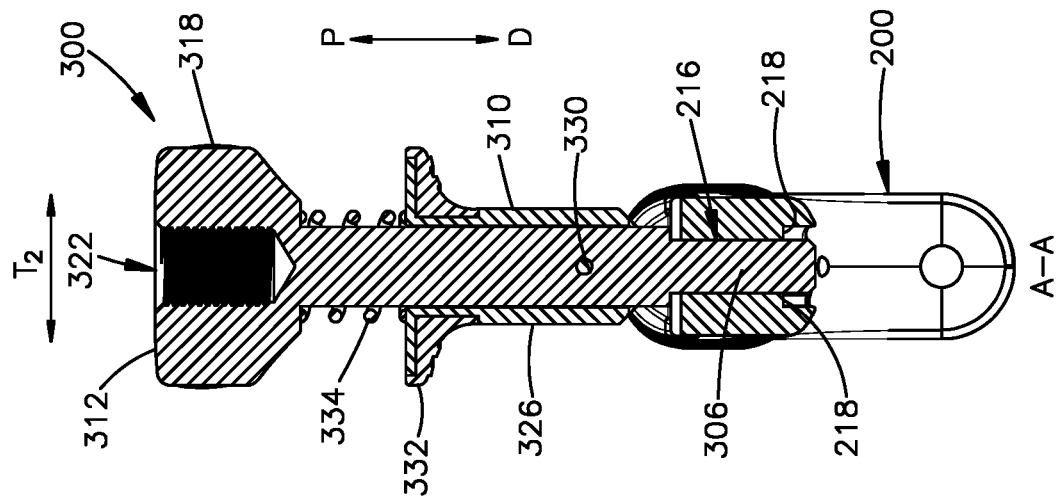
FIG. 8 shows a cross-sectional view of the system of FIGS. 1 and 2 taken along line A-A, with the strike instrument in a first rotational orientation.

During insertion of an intramedullary nail, an insertion handle is commonly affixed to the intramedullary nail, and the insertion handle is grasped by a medical professional so as to guide the intramedullary nail into a medullary canal of a bone. To drive the intramedullary nail into the medullary canal, a strike instrument can be attached to the insertion handle, and the medical professional can impact the strike instrument with an impaction instrument such as a hammer or mallet. The strike instrument transfers the impaction force from the impacting instrument to the insertion handle, which in turn transfers the impaction force to the intramedullary nail so as to drive the intramedullary nail into the medullary canal. Commonly, strike instruments are attached to insertion handles via threaded connections. However, the impaction force from the impaction instrument can loosen the threaded connection between a strike instrument and an insertion handle, and in some cases, damage the threaded connection. The following discussion relates to a strike instrument, and system including the same, that attaches to an insertion handle using a connection other than a threaded connection. The connection can remain secure during impact and can be less susceptible to damage from impaction force than a threaded connection.

Referring generally to FIGS. 1 to 28, and with particular attention to FIGS. 1, 9, 17, and 20, according to various embodiments, an intramedullary nail insertion system (10, 20, 30, 40) is configured to support insertion of an intramedullary nail 100 (shown in FIG. 28) into a medullary canal of a long bone. The intermedullary nail insertion system (10, 20, 30, and 40) comprises an insertion handle (200, 400, 600, 800) and a strike instrument (300, 500, 700, 900). The insertion handle (200, 400, 600, 800) removably couples to the intramedullary nail 100, and is configured to be grasped by a medical professional so as to guide the intramedullary nail 100 into the medullary canal of the long bone. The strike instrument (300, 500, 700, 900) removably couples to the insertion handle (200, 400, 600, 800). In some embodiments, the intramedullary nail insertion system 10 can include the intramedullary nail 100, although it will be understood that the intramedullary nail 100 can be distributed separately from the insertion handle (200, 400, 600, 800) and the strike instrument (300, 500, 700, 900), and that the insertion handle (200, 400, 600, 800) and the strike instrument (300, 500, 700, 900) can be distributed separately from one another.

In general, the strike instrument (300, 500, 700, 900) is configured to quickly couple to, and quickly decouple from, the insertion handle (200, 400, 600, 800). The strike instrument (300, 500, 700, 900) has a proximal end (302, 502) and a distal end (304, 504) that is opposite the proximal end (302, 502) along a distal direction D. As used herein, the term "proximal end" refers to an end that is closer to the medical professional during the medical procedure than the distal end, and the term "distal end" refers to an end that is further from the medical professional during the medical procedure than the proximal end. Further, the term "proximal direction" refers to a direction that extends towards the medical professional during the medical procedure, while the term "distal direction" refers to a direction that extends away from the medical professional during the medical procedure. In some embodiments, the proximal and distal directions referred to herein can coincide with the anatomical proximal and distal directions of a patient's limb, respectively, such as in an antegrade approach where the intramedullary nail is inserted in an anatomical proximal end of a limb. However, embodiments of the disclosure are not so limited. Thus, in other embodiments, the proximal and distal directions referred to herein can coincide with the anatomical distal and proximal directions, respectively, such as in a retrograde approach where the intramedullary nail is inserted into an anatomical distal end of a limb.

The strike instrument (300, 500, 700, 900) comprises a shaft (306, 506) and an abutment (308, 508). The shaft (306, 506) can extend between the proximal end (302, 502) and the distal end (304, 504) along a shaft axis $A_S$ that extends along a distal direction D. The abutment (308, 508) extends outward relative to the shaft (306, 506) along a first direction $D_1$, such as radially out from the shaft (306, 506). The strike instrument (300, 500, 700, 900) is configured such that rotation of the shaft (306, 506) about the shaft axis $A_S$ causes a corresponding rotation of the abutment (308, 508). In some examples, the abutment (308, 508) can be disposed adjacent the distal end (304, 504) of the strike instrument (300, 500, 700, 900). The abutment (308, 508) can define a length l and a width w in a plane that is perpendicular to the shaft axis $A_S$. The length l can extend along the first direction $D_1$, and the width can extend along a second direction $D_2$, perpendicular to the first direction $D_1$. The length l can be greater than a cross-sectional dimension of the shaft (306, 506) in the first direction $D_1$. In at least some embodiments, the length l can be greater than the width w. The abutment (308, 508) can be devoid of threading that is configured to engage the insertion handle (200, 400, 600, 800).

The shaft (306, 506) can be configured to rotate the abutment (308, 508) between a first rotational orientation (e.g., shown in FIGS. 1, 9, 17, 20) relative to the insertion handle (200, 400, 600, 800) and a second rotational orientation (e.g., shown in FIGS. 2, 10, 18, and 21) relative to the insertion handle (200, 400, 600, 800). The abutment (308, 508) can have a keyed relationship with a locking hole (216, 416, 616) of the insertion handle (200, 400, 600, 800). Thus, the abutment (308, 508) is configured to be received in the locking hole (216, 416, 616) and rotated relative to the locking hole (216, 416, 616) so as to lock the abutment (308, 508) within the locking hole (216, 416, 616). The abutment (308, 508) is shaped such that, when the abutment (308, 508)

is oriented in the first rotational orientation relative to the insertion handle (200, 400, 600, 800), the abutment (308, 508) can be inserted into, and removed from, locking hole (216, 416, 616) in the insertion handle (200, 400, 600, 800). Further, the abutment (308, 508) is shaped such that, when the abutment (308, 508) is received into the locking hole (216, 416, 616) of the insertion handle (200, 400, 600, 800) and is rotated to the second rotational orientation relative to the insertion handle (200, 400, 600, 800), the abutment (308, 508) engages an inner surface (218, 418, 618) of the insertion handle (200, 400, 600, 800) so as to define an interference with the inner surface (218, 418, 618) of the insertion handle (200, 400, 600, 800). The interference prevents the strike instrument (300, 500, 700, 900) from being removed from the insertion handle (200, 400, 600, 800) along a proximal direction P, opposite the distal direction D. In at least some embodiments, the strike instrument (300, 500, 700, 900) can be rotated between the first rotational orientation and the second rotational orientation by rotating the shaft (306, 506), and consequently the abutment (308, 508), by 360 degrees or less, such as by 270 degrees or less, such as by 180 degrees or less, such as by 135 degrees or less, such as by 100 degrees or less. In a preferred embodiment, the strike instrument (300, 500, 700, 900) can be rotated between the first rotational orientation and the second rotational orientation by rotating the shaft (306, 506), and consequently the abutment (308, 508), by approximately 90 degrees.

The strike instrument (300, 500, 700, 900) comprises a lock (310, 510, 710, 910) that is configured such that, when the abutment (308, 508) is received through the locking hole (216, 416, 616) in the insertion handle (200, 400, 600, 800) and is rotated to the second rotational orientation, the lock (310, 510, 710, 910) engages the insertion handle (200, 400, 600, 800) so as to prevent the abutment (3008, 508) from rotating from the second rotational orientation to the first rotational orientation. For example, the lock (310, 510, 710, 910) can include at least one of a protrusion (324, 724) and a recess (925) that is configured to engage another of a recess (220, 620) and a protrusion (425) of the handle (200, 400, 600, 800). The lock (310, 510, 710, 910) engages the insertion handle (200, 400, 600, 800) so as to prevent the shaft (306, 506), and hence the abutment (308, 508), from being rotated from the second rotational orientation to the first rotational orientation. Thus, the lock (310, 510, 710, 910) prevents the abutment (308, 508) from rotating to the first rotational orientation, thereby preventing the strike instrument (300, 500, 700, 900) from being removed from the insertion handle (200, 400, 600, 800) along the proximal direction P. The lock (310, 510, 710, 910) can be a releasable lock in that the lock (310, 510, 710, 910) can be released from engagement with the insertion handle (200, 400, 600, 800) so as to permit the abutment (308, 508) to rotate to the first rotational orientation, thereby allowing the strike instrument (300, 500, 700, 900) to be removed from the insertion handle (200, 400, 600, 800) along the proximal direction P. Thus, the lock (310, 510, 710, 910) can be configured to move between a locked position, wherein the lock (310, 510, 710, 910) prevents the abutment (308, 508) from rotating to the first rotational orientation, and an unlocked position, wherein the abutment (308, 508) is permitted to rotate to the first rotational orientation.

Figure 18:
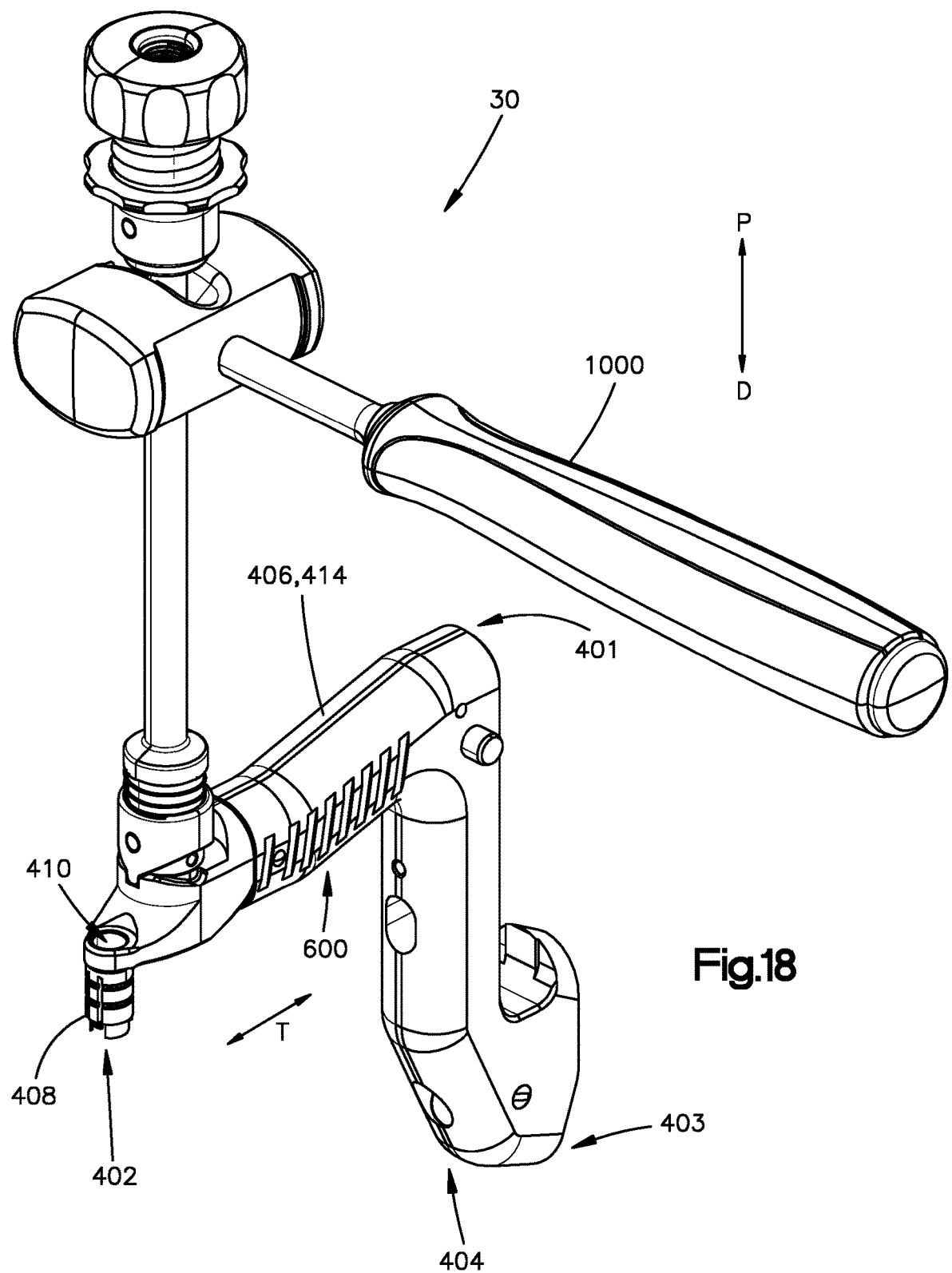
FIG. 18 shows an assembled perspective view of the system of FIG. 17 and an impaction tool, where the strike instrument is coupled to the insertion handle.

The strike instrument (300, 500, 700, 900) is configured to be impacted by an impaction tool (e.g., 1000 in FIG. 18) such as a hammer or mallet. In one example, the impaction tool can be configured to be guided along the shaft (306, 506) as illustrated in FIG. 18. The strike instrument (300, 500, 700, 900) is configured to transfer an impaction force from the tool to the insertion handle (200, 400, 600, 800), and the insertion handle (200, 400, 600, 800) is configured to transfer the impaction force from the strike instrument (300, 500, 700, 900) to the intramedullary nail 100 so as to drive the intramedullary nail 100 into the medullary canal. The strike instrument (300, 500, 700, 900) comprises a strike surface (312, 512, 513, 912) that is fixed to the shaft (306, 506). The strike surface (312, 512, 513, 912) can be translatably fixed such that movement of the strike surface (312, 512, 513, 912) along the distal direction D causes a corresponding translation of the shaft (306, 506) along the distal direction. Thus, when the strike surface (312, 512, 513, 912) is impacted by the tool along the distal direction D, movement of the strike surface (312, 512, 513, 912) along the distal direction D causes a corresponding movement of the shaft (306, 506) along the distal direction D.

Referring now more specifically to the details of the embodiment of FIGS. 1 to 8, and with specific reference to FIGS. 3 to 5, the strike instrument 300 has an abutment 308 that can include a first abutment end 308a and a second abutment end 308b that are opposite from one another. The abutment 308 can have a first abutment side 308c and a second abutment side 308d that are opposite from one another. The first and second abutment sides 308c and 308d can extend between the first and second abutment ends 308a and 308b. The first and second abutment ends 308a and 308b can extend between the first and second abutment sides 308c and 308d. The abutment 308 can extend outwards relative to the shaft 306 in opposed directions to the first abutment end 308a and the second abutment end 308b. The abutment 308 can have a length l along a first direction $D_1$ that extends from the first abutment end 308a to the second abutment end 308b, and a width w along a direction $D_2$ that extends from the first abutment side 308c to the second abutment side 308d. The length l can be greater than the width w. Thus, the abutment 308 can be elongate from the first abutment end 308a to the second abutment end 308b. The length l can be greater than a cross-sectional dimension of the shaft 306 that extends along the first direction $D_1$ from first abutment end 308a to the second abutment end 308b.

The abutment 308 can include at least one engagement surface 314 that is configured to engage an inner surface 218 (labeled in FIG. 8) of the handle 200 so as to define an interference with the inner surface 218 when the abutment is in the second rotational orientation. For example, the abutment 308 can include a first engagement surface 314 that extends from the shaft 306 to the first abutment end 308a, and a second engagement surface 314 that extends from the shaft 306 to the second abutment end 308b. Each engagement surface 314 can face towards the proximal direction P.

FIGS. 1 to 8 show an embodiment where the abutment 308 includes at least one protrusion that extends outward from the shaft 306 away from the central axis $A_S$. For example, the at least one protrusion can include first and second protrusions 316a and 316b that extend away from opposed sides of the shaft 306 along opposing directions. The first protrusion 316a can extend from the shaft 306 to the first side 308a, and the second protrusion 316b can extend from the shaft 306 to the second side 308b. The first and second sides 308a and 308b, and hence the first and second protrusions 316a and 316b, can be aligned along the first direction $D_1$. It will be understood that the abutment can have other shapes, for example, as discussed in further detail below in relation to FIGS. 9 to 17.

The strike instrument 300 can include a force transfer surface 320 that is translatably fixed relative to the shaft 306 such that translation of the shaft 306 along the distal direction D causes a corresponding translation of the force transfer surface 320. The force transfer surface 320 is configured to engage the insertion handle 200 so as to transfer the impaction force from the strike instrument 300 to the handle 200. The force transfer surface 320 can face towards the distal direction D. In at least some examples, the force transfer surface 320 can oppose the at least one engagement surface 314 of the abutment 308. For instance, the force transfer surface 320 can face the at least one engagement surface 314 of the abutment 308. The force transfer surface 320 can define a shoulder of the shaft 306. The shoulder can adjoin a first or proximal portion 306a of the shaft 306 to a second or distal portion 306b of the shaft 306, the first portion 306a having a cross-sectional dimension that is greater than that of the second portion 306a so as to define the shoulder. In other examples, the force transfer surface 320 can define the distal-most end surface of the strike instrument 300, such as a distal-most end surface of the shaft 306.

The strike surface 312 can be disposed at the proximal end 302 of the strike instrument 300. In one example, the strike instrument 300 can include a knob 318 that defines the strike surface 312. The knob 318 can be disposed at the proximal end 302 of the strike instrument 300. The knob 318 can be rotationally fixed to the shaft 306. Thus, the strike instrument 300 can be configured such that rotation of the knob 318 causes a corresponding rotation of the shaft 306. The strike surface 312 can define a proximal-most surface of the strike instrument 300. The knob 318 can have a cross-sectional dimension along a select transverse direction $T_s$ that is greater than a cross-sectional dimension of the shaft 306 along the select transverse direction $T_s$. The select transverse direction $T_s$ can be perpendicular to the distal direction D. The knob 318 can define a grip that is configured to be grasped by a medical professional so as to rotate the shaft 306 between the first rotational orientation and the second rotational orientation.

The proximal end 302 of the strike instrument 300 can include a fastener 322 that is configured to attach to a back-out instrument (not shown). In one example, the fastener 322 can be a threaded bore. When attached to the fastener 322, the back-out instrument can be struck along the proximal direction P so as to back the intramedullary nail 100 at least partially out of the medullary canal. The back-out instrument can be used when, for example, the intramedullary nail 100 is inadvertently driven too far into the medullary canal.

The lock 310 includes at least one protrusion 324 that is configured to engage at least one recess 220 of the handle 200 so as to prevent the shaft 306, and hence the abutment 308, from being rotated from the second rotational orientation to the first rotational orientation when the abutment 308 is received in the locking hole 216 of the handle 200. The at least one protrusion 324 can include a pair of protrusions 324 that are offset from one another. In one example, the protrusions 324 can be opposite one another on opposed sides of the shaft axis $A_S$. It will be understood that, in alternative embodiments, the lock 310 can additionally, or alternatively, define at least one recess (for example, as discussed below in relation to FIGS. 9 to 16) that is configured to engage at least one protrusion of the handle 200.

The lock 310 can include a locking body 326 that includes the at least one protrusion 324. In one example, as shown, the locking body 326 can be a sleeve, although it will be understood that the locking body 326 can have any other suitable shape. The locking body 326 can have a proximal end 326a and a distal end 326b. The locking body 326 can define a channel 327 therethrough that extends from the proximal end 326a to the distal end 326b. The channel 327 can be configured to receive the shaft 306 therethrough such that the shaft 306 extends out of the proximal end 326a and the distal end 326b. The at least one protrusion 324 can extend from the distal end 326b along the distal direction D.

The locking body 326 can be rotationally fixed to the shaft 306 such that rotation of the shaft 306 causes a corresponding rotation of the locking body 326. The locking body 326 can be configured to translate relative to the shaft 306 along the proximal and distal directions P and D such that the lock 310 can be transitioned between a locked position and an unlocked position, wherein the protrusion 324 projects further along the distal direction D in the locked position than in the unlocked position. In the locked position, the protrusion can be received in the recess 220 of the handle 200, and in the unlocked position, the protrusion 324 can be removed from the recess 220 of the handle 200. It will be understood that the locking body 326 can have another suitable shape, other than a sleeve, that is configured to move along the proximal and distal directions P and D relative to the shaft 306 and carry the protrusion 324 between the locked and unlocked positions.

The lock 310 can include a fastener that couples the locking body 326 to the shaft 306 such that the locking body 326 is rotationally fixed to the shaft 306 and translatable relative to the shaft 306 along the proximal and distal directions P and D. In one example, the fastener can include a pin 330 that extends radially from, and is positionally fixed to, one of the shaft 306 and the locking body 326. The pin 330 can be received in a slot 328 of another one of the shaft 306 and the locking body 326. The slot 328 can be elongate along the proximal and distal directions P and D. The pin 330 can be configured to translate in the slot 328 along the proximal and distal directions P and D so as to allow the locking body 326 to translate along the proximal and distal directions P and D.

In the embodiment of FIGS. 1 to 8, the locking body 326 defines the slot 328, and the pin 330 extends radially outward from, and is positionally fixed to, the shaft 306. The pin 330 and slot 328 are configured such that, when the pin 330 is disposed in the slot 328, the pin 330 can translate within the slot 328 along the proximal and distal directions P and D, thereby allowing the locking body 326 to translate along the proximal and distal directions P and D relative to the shaft 306. The pin 330 and slot 328 can be configured such that, when the pin 330 is disposed in the slot 328, the pin 330 limits, or prevents altogether, rotation of the locking body 326 relative to the shaft 306. The slot 328 can have a proximal end 328a that is configured to engage the pin 330 so as to limit movement of the locking body 326 along the distal direction D. The slot 328 can have a distal end 328b that is configured to engage the pin 330 so as to limit movement of the locking body 326 along the proximal direction P. Thus, the proximal end 328a and the distal end 328b can act as stops so as to limit movement of the locking body 326 along the proximal and distal directions P and D.

The lock 310 can include a flange 332 that is configured to be engaged by fingers or a hand of a user such as a medical professional so as to move the lock 310 from the locked position to the unlocked position along the proximal direction P. The flange 332 can extend outwardly from the locking body 326. In one example, the flange 332 can extend from the proximal end 326a of the locking body 326, although in alternative embodiments, the flange 332 can extend anywhere between the proximal and distal ends 326a and 326b of the locking body 326. The locking body 326 can have a cross-sectional dimension along a select transverse direction that is perpendicular to the shaft axis $A_s$, and the flange 332 can have a flange cross-sectional dimension along the select transverse direction that is greater than the cross-sectional dimension of the locking body 326. A distal or bottom end of the flange 332 can be configured to receive the fingers of a user such as a medical professional. Thus, moving the fingers against the distal or bottom end along the proximal direction P can cause the flange 332, and consequently the locking body 326, to be moved along the proximal direction P from the locked position to the unlocked position.

The locking body 326 can be biased in the distal direction D towards the locked position. In other words, a biasing force can be applied to the locking body 326 to cause the locking body 326 to be biased in the distal direction D. For example, the lock 310 can include a spring 334 that biases the locking body 326 towards the locked position. The spring 334 can be a coil spring, such as a compression spring, an elastomeric material, or any other suitable spring that can bias the locking body 326 along the distal direction D. The spring 334 can be disposed between the locking body 326 and the knob 318. The spring 334 can engage the knob 318 and the locking body 326, such as the proximal end 326a of the locking body 326, so as to bias the locking body 326 along the distal direction D. The spring 334 can define a channel therethrough that receives the shaft 306 such that the spring 334 is disposed between the locking body 326 and the knob 318.

Referring now more specifically to FIGS. 1, 2, and 6 to 8, the handle 200 has a first end portion 202 and a second end portion 204 that are offset from one another along a select transverse direction T. The handle 200 has an upper end 210, and a lower end 203 that is offset from the upper end 210 along the distal direction D. The select transverse direction T can be a radial direction that extends radially out from the intramedullary nail 100 when the handle 200 is coupled to the intramedullary nail 100. The handle 200 has an outer surface 206 between the first end portion 202 and the second end portion 204 that defines a grip 214 configured to be gripped by a medical professional during insertion of the intramedullary nail 100. In one example, the grip 214 can have a generally cylindrical shape that extends along the select transverse direction T.

The first end portion 202 can include a coupler 208 that is configured to couple the handle 200 to the intramedullary nail 100. In at least some embodiments, the coupler 208 can be configured to couple the handle 200 to the intramedullary nail 100 such that the handle 200 and intramedullary nail 100 are rotationally fixed relative to one another. The first end portion 202 can define a cannulation 210 that extends through the first end portion 202 along the distal direction D. The cannulation 210 can be configured (e.g., sized and shaped) so as to receive a rod, such as a reaming rod, therein as the handle 200 guides the intramedullary nail 100 along the rod into the medullary canal of the bone. The cannulation 210 can be configured such that it is aligned with a cannulation of the intramedullary nail 100 when the handle 200 is coupled to the intramedullary nail 100. The cannulation 210 can extend through the coupler 208.

The handle 200 has a receptacle 212 that is configured to receive at least a portion of the strike instrument 300 so as to couple the strike instrument 300 to the handle 200. In one example, the receptacle 212 can be disposed at the first end portion 202 of the handle 200. For example, the receptacle 212 can be disposed between the coupler 208 and the grip 214 with respect to the select transverse direction T, although alternative locations are contemplated. The receptacle 212 can define a locking hole 216 that extends into the upper end 201 towards the lower end 203 along the distal direction D along a receptacle axis $A_R$. The locking hole 216 can be configured to receive a portion of the strike instrument, such as the abutment 308 and at least a portion of the shaft 306 of the strike instrument 300.

The locking hole 216 can include a proximal portion 216a, and a distal portion 216b that is offset from the proximal portion 216a along the distal direction D. The proximal portion 216a can have a length $l_1$ along a first transverse direction $T_1$ that is transverse to the receptacle axis $A_R$, and a width $w_1$ along a second transverse direction $T_2$ that is perpendicular to the receptacle axis $A_R$ and the first transverse direction $T_1$. The length $l_1$ of the proximal portion 216a can be greater than the width $w_1$ of the proximal portion 216b. Thus, the proximal portion 216a can be elongate along the first transverse direction $T_1$. The distal portion 216b can have a width $w_2$ along the second transverse direction $T_2$ that is greater than the width $w_1$ of the proximal portion 216a. The locking hole 216 can have an inner surface 218 that defines a shoulder of the locking hole 216 that adjoins the proximal portion 216a to the distal portion 216b. The inner surface 218 can face towards the distal direction D.

Figure 7:
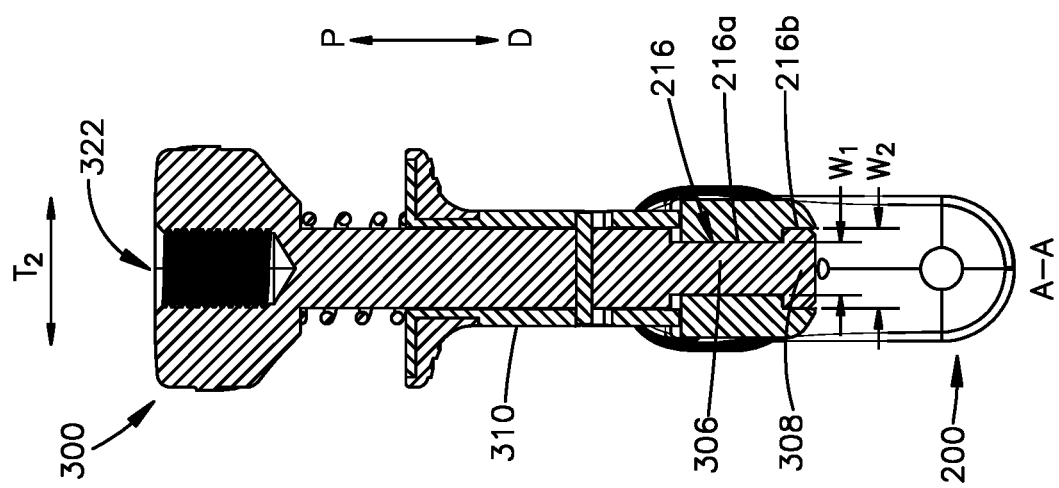
FIG. 7 shows a cross-sectional view of the system of FIGS. 1 and 2 taken along line A-A, with the strike instrument in a second rotational orientation.
Figure 6:
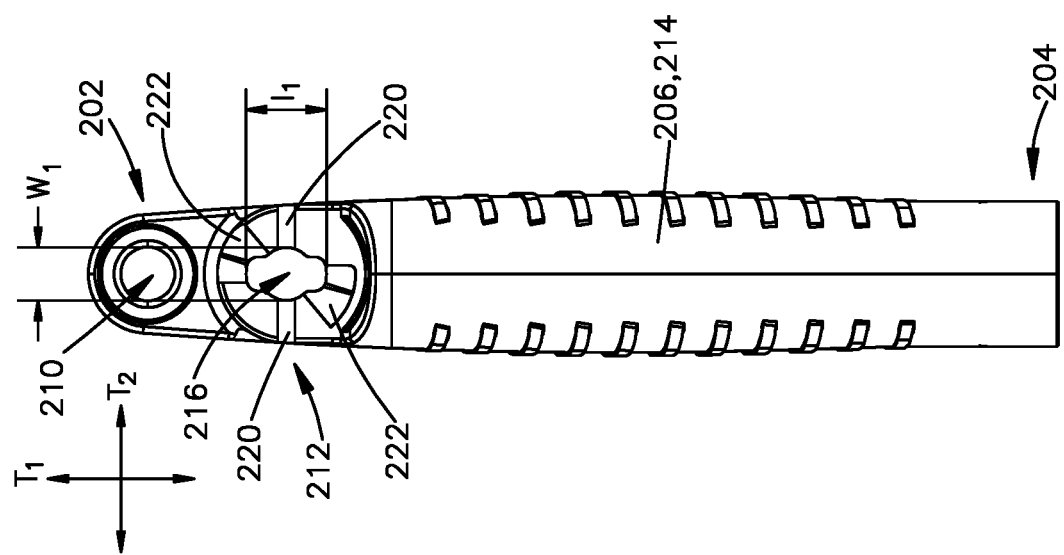
FIG. 6 shows a top plan view of the insertion handle of FIGS. 1 and 2 according to one embodiment.

The locking hole 216 can be sized and shaped to receive the abutment 308 through the proximal portion 216a of the locking hole 216 and into the distal portion 216b of the locking hole 216 when the abutment 308 is in the first rotational orientation relative to the insertion handle 200 (as shown in FIG. 8). For example, the length $l_1$ and width $w_1$ of the proximal portion 216a of the locking hole 216 can be greater than the length l and width w of the abutment 308, respectively. The locking hole 216 can be sized and shaped to lock the abutment 308 within the distal portion 216b when the abutment 308 is in the second rotational orientation relative to the insertion handle 200 (as shown in FIG. 7) so as to fix the strike instrument 300 to the insertion handle 200 with respect to translation along the proximal and distal directions P and D. For example, the width $w_1$ of the proximal portion 216a of the locking hole 216 can be less than the length l of the abutment 308, and the width $w_2$ of the distal portion 216b of the locking hole 216 can be greater than the length l of the abutment 308. When the abutment 308 is in the second rotational orientation relative to the insertion handle 200 (as shown in FIG. 7), the abutment 308 can abut the inner surface 218 of the insertion handle 200 so as to prevent the abutment 308, and consequently the strike instrument 300, from being moved relative to the insertion handle 200 along the proximal direction P.

The receptacle 212 can define at least one recess 220 that extends into an upper surface of the insertion handle 200. In some embodiments, the at least one recess 220 can comprise first and second recesses 220. The first and second recesses 220 can be disposed on opposed sides of the locking hole 216. The at least one recess 220 is configured to receive at least one protrusion 324 of the lock 310 when the strike instrument 300 is in the second rotational orientation relative to the insertion handle 200 so as to rotationally fix the strike instrument 300 to the insertion handle 200. When the at least one recess 220 receives the at least one protrusion 324, inner walls of the insertion handle 200 that define the at least one recess 220 interfere with the protrusion 324 so as to prevent the lock 310, and hence the strike instrument 300, from being rotated about the shaft axis $A_S$ relative to the insertion handle 200.

The insertion handle 200 can include at least one ramped surface 222 adjacent to the at least one recess 220. The at least one ramped surface 222 can be ramped towards the proximal direction P as it extends towards the at least one recess 220. The at least one ramped surface 222 can extend about a portion of the locking hole 216 towards the at least one recess along one of a clockwise and a counter clockwise direction. The at least one ramped surface 222 can be configured to guide the at least one protrusion 324 of the lock 310 to ride up the ramped surface 222 as the strike instrument 300 is rotated from the first orientation to the second orientation, thereby causing the lock 310 to retract along the proximal direction P. Retraction of the lock 310 in the proximal direction P can compress the spring 334. When the at least one protrusion 324 is aligned with the at least one recess 220, the biasing force of the lock 310 biases the at least one protrusion 324 in the distal direction D into the at least one recess 220, thereby rotationally fixing the strike instrument 300 to the insertion handle 200.

In operation, and with reference to FIGS. 1, 2, 7, and 8, a method can comprise a step of orienting the abutment 308 of the strike instrument 300 in a first rotational orientation so as to align the abutment 308 with the locking hole 216 of the insertion handle 200. The method can comprise a step of moving the strike instrument 300 along the distal direction D so as to insert the abutment 308 through the proximal portion 216a of the locking hole 216 and into the distal portion 216b of the locking hole 216. The method can comprise a step of rotating the strike instrument 300 from the first orientation to the second rotational orientation. The rotating step can comprise rotating the shaft 306 so as to cause the abutment 308 to rotate such that the abutment 308 engages an inner surface 218 of the locking hole 216, thereby preventing the strike instrument 300 from being removed from the insertion handle 200 along the proximal direction P. The method can comprise a step of locking the strike instrument 300 in the second rotational orientation relative to the insertion handle 200. The locking step can comprise a step of rotating the lock 310 so as to cause the at least one protrusion 324 of the lock 310 to engage the at least one recess 220 of the insertion handle 200 so that the walls of the at least one recess 220 interfere with the at least one protrusion 324, thereby preventing the lock 310 from being rotated relative to the insertion handle 200. The step of rotating the lock 310 can occur concurrently with the step of rotating the abutment 308. The method can comprise a step of impacting the strike surface 312 of the strike instrument 300 with a tool so as to drive the intramedullary nail 100 into the medullary canal.

To remove the strike instrument 300, the method can comprise a step of translating the locking body 326 of the lock 310 along the proximal direction P so as to disengage the at least one protrusion 324 of the lock 310 from the at least one recess 220 of the insertion handle 200. In performing the translating step, a medical professional can engage the locking body 326 with a hand (e.g., by placing fingers under the flange 332 of the locking body 326) and move the locking body 326 along the proximal direction P. The method can comprise a step of rotating the strike instrument 310 from the second rotational orientation to the first rotational orientation such that the interference between the abutment 308 and the inner surface 218 of the insertion handle 200 is removed. The method can comprise a step of translating the strike instrument 300 along the proximal direction P so as to remove the abutment 308 from the locking hole 216 of the insertion handle 200.

Turning now to FIGS. 9 to 16, an embodiment is shown in which the shaft 506 has a length along the shaft axis $A_s$ that is greater than the length of the shaft 506 in the embodiment of FIGS. 1 to 8, and the lock 510 includes an actuator 536 that is configured to move the lock 510 from the locked position to the unlocked position. With specific reference to FIGS. 12 to 14, similar to the embodiment of FIGS. 1 to 8, the abutment 508 can include a first abutment end 508a and a second abutment end 508b that are opposite from one another. The abutment 508 can have a first abutment side 508c and a second abutment side 508d that are opposite from one another. The first and second abutment sides 508c and 508d can extend between the first and second abutment ends 508a and 508b. The first and second abutment ends 508a and 508b can extend between the first and second abutment sides 508c and 508d. The abutment 508 can extend outwards relative to the shaft 506 in opposed directions to the first abutment end 508a and the second abutment end 508b. The abutment 508 can have a length l along a direction that extends from the first abutment end 508a to the second abutment end 508b, and a width w along a direction that extends from the first abutment side 508c to the second abutment side 508d. The length l can be greater than the width w. Thus, the abutment 508 can be elongate from the first abutment end 508a to the second abutment end 508b. The length l can be greater than a cross-sectional dimension of the shaft 506 that extends along the direction from first abutment end 508a to the second abutment end 508b.

The abutment 508 can include at least one engagement surface 514 that is configured to engage an inner surface 418 (labeled in FIG. 16) of the handle 400 so as to define an interference with the inner surface 418 when the abutment is in the second rotational orientation. For example, the abutment 508 can include a first engagement surface 514 that extends from the shaft 506 to the first abutment end 508a, and a second engagement surface 514 that extends from the shaft 506 to the second abutment end 508b. Each engagement surface 514 can face towards the proximal direction P.

FIGS. 9 to 16 show an embodiment where the abutment 508 is a single protrusion that extends from a distal end of the shaft 506 along the distal direction D and along a transverse direction that is perpendicular to the distal direction D. The protrusion includes the first and second abutment ends 508a and 508b. The first and second abutment ends 508a and 508b can be aligned along the first direction $D_1$. It will be understood that the abutment 508 can have other shapes suitable for locking the abutment 508 within a locking hole of an insertion handle.

The strike instrument 500 can include a force transfer surface 520 (labeled in FIG. 13) that is translatably fixed relative to the shaft 506 such that translation of the shaft 506 along the distal direction D causes a corresponding translation of the force transfer surface 520. The force transfer surface 520 is configured to engage the handle 400 so as to transfer the impaction force from the strike instrument 500 to the handle 400. The force transfer surface 520 can face towards the distal direction D. In at least some examples, the force transfer surface 520 can oppose the at least one engagement surface 514 of the abutment 508. The force transfer surface 520 can define a shoulder of the shaft 506. The shoulder can adjoin a proximal portion 506a (labeled in FIG. 14) of the shaft 506 to a distal portion 506b (labeled in FIG. 14) of the shaft 506, the proximal portion 506a having a cross-sectional dimension that is greater than that of the distal portion 506a so as to define the shoulder. In other examples, the force transfer surface 520 can define the distal-most end surface of the strike instrument 500, such as a distal-most end surface of the abutment 508.

The strike surface 512 can be disposed at the proximal end 502 of the strike instrument 500. The strike instrument 500 can include a knob 518 that defines the strike surface 512. The knob 518 can be disposed at the proximal end 502 of the strike instrument 500. The knob 518 can be rotationally fixed to the shaft 506. Thus, the strike instrument 500 can be configured such that rotation of the knob 518 causes a corresponding rotation of the shaft 506. The strike surface 512 can define a proximal-most surface of the strike instrument 500. The knob 518 can have a cross-sectional dimension along a select transverse direction $T_s$ that is greater than a cross-sectional dimension of the shaft 506 along the select transverse direction $T_s$. The selection transverse direction $T_s$ can be perpendicular to the distal direction D. The knob 518 can define a grip that is configured to be grasped by a medical professional so as to rotate the shaft 506 between the first rotational orientation and the second rotational orientation.

The strike instrument 500 can additionally, or alternatively, include a strike surface 513 disposed between the proximal end 502 and the distal end 504 of the strike instrument 500. For example, the strike surface 513 can be disposed between the abutment 508 and a middle of the shaft 506 along the shaft axis $A_s$. The strike surface 513 is fixed to the shaft 506. The strike surface 513 can extend outward from the shaft 506 along a direction that is transverse to the shaft axis $A_s$. The strike surface 513 can be translatably fixed such that movement of the strike surface 513 along the distal direction D causes a corresponding translation of the shaft 506 along the distal direction. Thus, when the strike surface 513 is impacted by the tool along the distal direction D, movement of the strike surface 513 along the distal direction D causes a corresponding movement of the shaft 506 along the distal direction D. The shaft 506 can act as a guide to guide a tool 1000 to impact the strike surface 513 as shown in FIG. 18.

With reference to FIG. 9, the proximal end 502 of the strike instrument 500 can include a fastener 522 that is configured to attach to a back-out instrument (not shown). In one example, the fastener 522 can be a threaded bore. When attached to the fastener 522, the back-out instrument can be struck along the proximal direction P so as to back the intramedullary nail 100 at least partially out of the medullary canal. The back-out instrument can be used when, for example, the intramedullary nail 100 is inadvertently driven too far into the medullary canal.

Figure 14:
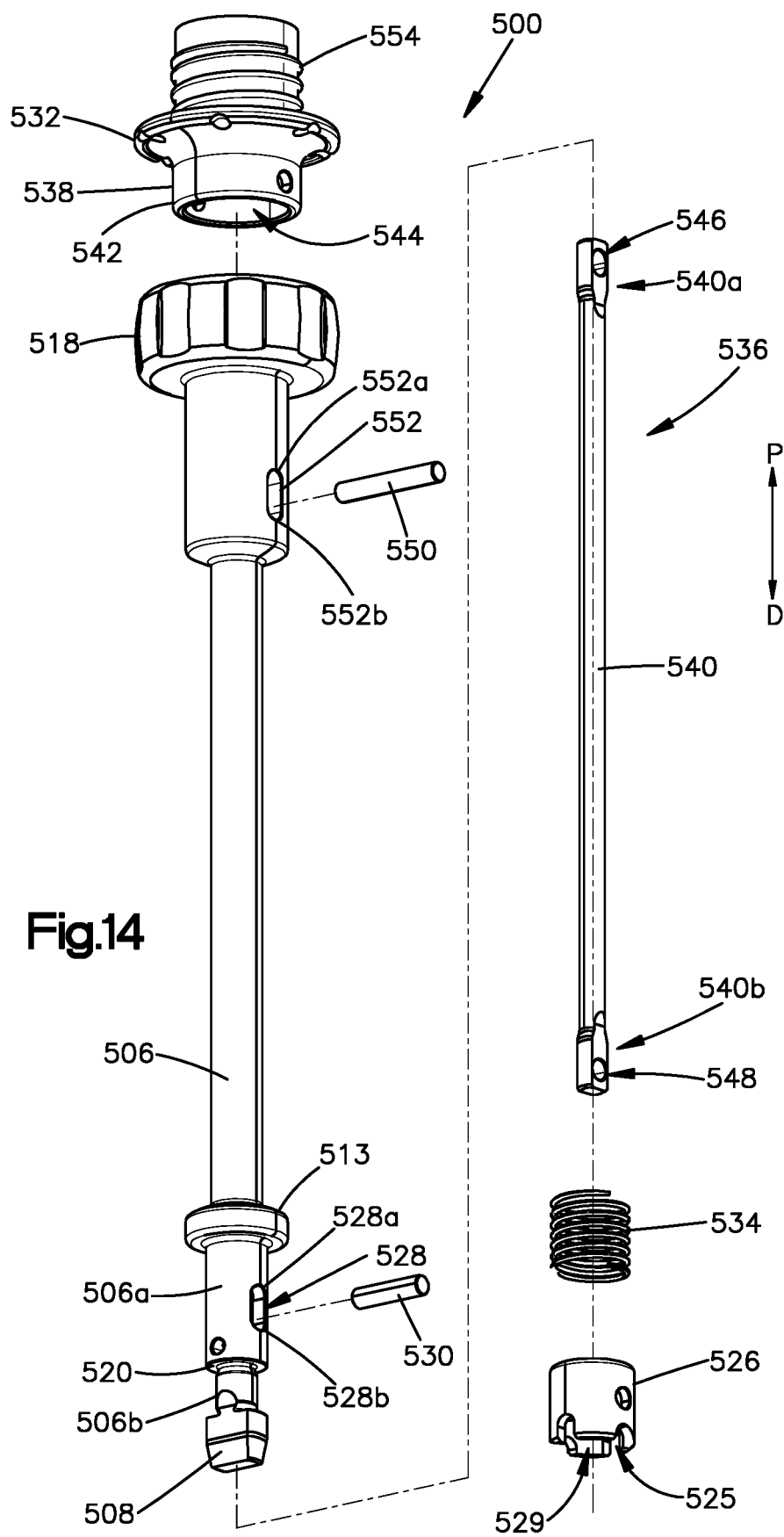
FIG. 14 shows an exploded perspective view of the strike instrument of FIG. 12.
Figure 16:
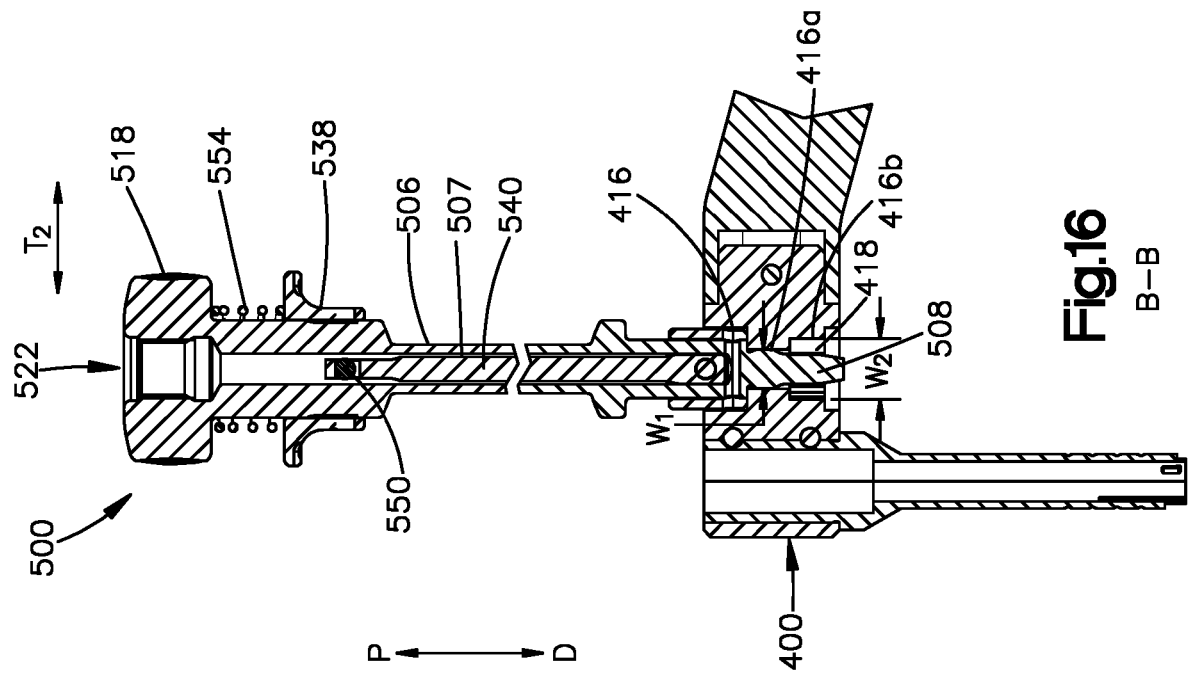
FIG. 16 shows a cross-sectional view of the system of FIGS. 9 and 10 taken along line B-B, with the strike instrument in a first rotational orientation.

Turning to FIGS. 12 to 14, the lock 510 includes at least one recess 525 that is configured to engage at least one protrusion 425 of the handle 400 so as to prevent the shaft 506, and hence the abutment 508, from being rotated from the second rotational orientation to the first rotational orientation when the abutment 508 is received in the locking hole 416 of the handle 400. The at least one recess 525 can include a pair of recesses 525 that are offset from one another. In one example, the recesses 525 can be opposite one another on opposed sides of the shaft axis $A_S$.

The lock 510 can include a locking body 526 that defines the at least one recess 525. In one example, as shown, the locking body 526 can be a sleeve, although it will be understood that the locking body 526 can have any other suitable shape. The locking body 526 can have a proximal end 526a and a distal end 526b. The locking body 526 can define a channel 529 therethrough that extends from the proximal end 526a to the distal end 526b. The channel 529 can be configured to receive the shaft 506 therethrough such that the shaft 506 extends out of the proximal end 526a and the distal end 526b. The at least one recess 525 can extend into the distal end 526b of the locking body 526 towards the proximal end 526a along the proximal direction P.

The locking body 526 can be rotationally fixed to the shaft 506 such that rotation of the shaft 506 cause a corresponding rotation of the locking body 526. The locking body 526 can be translatable relative to the shaft 506 along the proximal and distal directions P and D such that the lock 510 can be transitioned between a locked position and an unlocked position, wherein the recess 525 projects further along the distal direction D in the locked position than in the unlocked position. In the locked position, the at least one recess 525 receives the protrusion 425 of the handle 400, and in the unlocked position, the at least one recess 525 is removed from the protrusion 425 of the handle 400. It will be understood that the locking body 326 can have another suitable shape, other than a sleeve, that is configured to move along the proximal and distal directions P and D relative to the shaft 306 and carry the protrusion 324 between the locked and unlocked positions.

The lock 510 can include a fastener that couples the locking body 526 to the shaft 506 such that the locking body 526 is rotationally fixed to the shaft 506 and translatable relative to the shaft 506 along the proximal and distal directions P and D. In one example, the fastener can include a pin 530 that extends radially from, and is positionally fixed to, one of the shaft 506 and the locking body 526. The pin 530 can be received in a slot 528 of another one of the shaft 506 and the locking body 526. The pin 530 can be configured to translate in the slot 528 along the proximal and distal directions P and D so as to allow the locking body 526 to translate along the proximal and distal directions P and D.

In the embodiment of FIGS. 9 to 16, the shaft 506 defines the slot 528 that is elongate along the proximal and distal directions P and D, and the pin 530 that extends radially outward from the shaft 506, and is positionally fixed to the locking body 526. The pin 530 and slot 528 are configured such that, when the pin 530 is disposed in the slot 528, the pin 530 can translate within the slot 528 along the proximal and distal directions P and D, thereby allowing the locking body 526 to translate along the proximal and distal directions P and D relative to the shaft 506. The pin 530 and slot 528 can be configured such that, when the pin 530 is disposed in the slot 528, the pin 530 limits, or prevents altogether, rotation of the locking body 526 relative to the shaft 506. The slot 528 can have a proximal end 528a that is configured to engage the pin 530 so as to limit movement of the locking body 526 along the distal direction D. The slot 528 can have a distal end 528b that is configured to engage the pin 530 so as to limit movement of the locking body 526 along the proximal direction P. Thus, the proximal end 528a and the distal end 528b can act as stops so as to limit movement of the locking body 526 along the proximal and distal directions P and D.

With continued reference to FIGS. 12 to 14, the lock 510 includes an actuator 536 that is configured to move the locking body 526 from the locked position to the unlocked position. The actuator 536 can comprise a handle 538 and an actuator shaft 540 that couples the handle 338 to the locking body 326. The actuator 336 can be configured such that movement of the handle 338 along the proximal direction P causes the actuator shaft 540 to move along the proximal direction P, which in turn causes the locking body 526 to move along the proximal direction P from the locked position to the unlocked position.

In one example, as shown, the handle 538 can include a sleeve 542 and a flange 532 that extends outwardly from the sleeve 542, although it will be understood that the handle 538 can have any other suitable shape. The handle 538 can define a channel 544 therethrough that is configured to receive the shaft 506 therethrough such that the shaft 506 extends out of opposed ends of the handle 538. The flange 532 can be configured to be engaged by fingers or a hand of a user such as a medical professional so as to move the lock 510 from the locked position to the unlocked position along the proximal direction P. In one example, the flange 532 can extend from a proximal end of the sleeve 542, although in alternative embodiments, the flange 532 can extend anywhere between the proximal and distal ends of the sleeve 542. The sleeve 542 can have a cross-sectional dimension along a select transverse direction that is perpendicular to the shaft axis $A_s$, and the flange 532 can have a flange cross-sectional dimension along the select transverse direction that is greater than the cross-sectional dimension of the sleeve 542. A distal or bottom end of the flange 532 can be configured to receive the fingers of a user such as a medical professional. Thus, moving the fingers against the distal or bottom end along the proximal direction P can cause the flange 532, and consequently, the handle 538 to be moved along the proximal direction P.

The handle 538 can be translatable relative to the shaft 506 along the proximal and distal directions P and D. The actuator 536 can include a fastener that couples the handle 538 to the shaft 506 such that handle 538 is translatable relative to the shaft 506 along the proximal and distal directions P and D, and in some examples, rotationally fixed to the shaft 306.

The fastener can include a pin 550 that extends radially from, and is positionally fixed to, one of the shaft 506 and the handle 538. The pin 550 can be received in a slot 552 of another one of the shaft 506 and the handle 538. The slot 552 can be elongate along the proximal and distal directions P and D. The pin 550 can be configured to translate in the slot 552 along the proximal and distal directions P and D so as to allow the handle 538 to translate along the proximal and distal directions P and D.

In the embodiment of FIGS. 9 to 16, the shaft 506 defines the slot 552, and the pin 550 extends radially outward from, and is positionally fixed to, the handle 538. The pin 550 and slot 552 are configured such that, when the pin 550 is disposed in the slot 552, the pin 550 can translate within the slot 552 along the proximal and distal directions P and D, thereby allowing the handle 538 to translate along the proximal and distal directions P and D relative to the shaft 506. The pin 550 and slot 552 can be configured such that, when the pin 550 is disposed in the slot 552, the pin 550 limits, or prevents altogether, rotation of the handle 538 relative to the shaft 506. The slot 552 can have a proximal end 552a that is configured to engage the pin 550 so as to limit movement of the handle 538 along the distal direction D. The slot 552 can have a distal end 552b that is configured to engage the pin 550 so as to limit movement of the handle 538 along the proximal direction P. Thus, the proximal end 552a and the distal end 552b can act as stops so as to limit movement of the handle 538 along the proximal and distal directions P and D.

The actuator shaft 540 can have a proximal portion 540a and a distal portion 540b that are offset from one another along the shaft axis $A_s$. In one example, the shaft 506 can have a cannulation 507 (labeled in FIG. 15) that extends from the proximal end 502 of the shaft 506 towards the distal end 304 along the shaft axis $A_s$. The actuator shaft 540 can be received in the cannulation 507.

The proximal portion 540a of the actuator shaft 540 can be configured to couple the actuator shaft 540 to the handle 538 such that the handle 538 is translationally fixed to the actuator shaft 540 with respect to the proximal and distal directions P and D. For example, the proximal portion 540a can define a fastener 546 that is configured to couple to the pin 550. The fastener 546 can define an opening that is configured to receive the pin 550. The pin 550 fixes the actuator shaft 540 to the handle 538 with respect to translation along the proximal and distal directions P and D, and couples both the actuator shaft 540 and the handle 538 to the shaft 506 such that both the actuator shaft 540 and the handle 538 are translatable relative to the shaft 506 along the proximal and distal directions P and D.

Similarly, the distal portion 540b can be configured to couple to the actuator shaft 540 to the locking body 526 such that the locking body 526 is translationally fixed to the actuator shaft 540 with respect to the proximal and distal directions P and D. For example, the distal portion 540b can define a fastener 548 that is configured to couple to the pin 530. The fastener 548 can define an opening that is configured to receive the pin 530. The pin 530 fixes the actuator shaft 540 to the locking body 536 with respect to translation along the proximal and distal directions P and D, and couples both the actuator shaft 540 and the locking body 536 to the shaft 506 such that both the actuator shaft 540 and the locking body 536 are translatable relative to the shaft 506 along the proximal and distal directions P and D. Thus, movement of the handle 538 along the proximal direction P relative to the shaft 506 causes a corresponding movement of the actuator shaft 540 along the proximal direction P relative to the shaft 506, which in turn causes a corresponding movement of the locking body 536 along the proximal direction P relative to the shaft 506.

The locking body 526 can be biased in the distal direction D towards the locked position. In other words, a biasing force can be applied to the locking body 526 to cause the locking body 526 to be biased in the distal direction D. For example, the lock 510 can include a spring 554 that biases the locking body 526 towards the locked position. The spring 554 can be a coil spring, such as a compression spring, an elastomeric material, or any other suitable spring that can bias the locking body 526 along the distal direction D. The spring 554 can be disposed between the handle 538 and the knob 518. The spring 554 can engage the knob 518 and the handle 538, such as the proximal end of the handle 538, so as to bias the handle 538 along the distal direction D, thereby biasing the actuator shaft 540 and the locking body 526 along the distal direction D. The spring 554 can define a channel therethrough that receives the shaft 506 such that the spring 554 is disposed between the handle 538 and the knob 518.

In addition, or alternatively, the lock 510 can include a spring 534 (shown in FIG. 14) that biases the locking body 526 towards the locked position. The spring 534 can be a coil spring, such as a compression spring, an elastomeric material, or any other suitable spring that can bias the locking body 526 along the distal direction D. The spring 534 can be configured to engage the locking body 526 so as to bias the locking body along the distal direction D. In one example, the spring 534 can be disposed between the strike surface 513 and the locking body 526, such as the proximal end 526a of the locking body 526, so as to bias the locking body 526 along the distal direction D. The spring 534 can define a channel therethrough that receives the shaft 506 such that the spring 534 is disposed between the strike surface 513 and the locking body 526.

Referring now more specifically to FIGS. 9, 10, 11, and 15 to 16, the handle 400 can be implemented in a manner similar to the handle 400 of FIGS. 1 to 8, except that the handle 400 includes at least one protrusion 425 instead of at least one recess 420. The handle 400 has a first end portion 402 and a second end portion 404 that are offset from one another along a select transverse direction T. The handle 400 has an upper end 410, and a lower end 403 that is offset from the upper end 410 along the distal direction D. The select transverse direction T can be a radial direction that extends radially out from the intramedullary nail 100 when the handle 400 is coupled to the intramedullary nail 100. The handle 400 has an outer surface 406 between the first end portion 402 and the second end portion 404 that defines a grip 414 configured to be gripped by a medical professional during insertion of the intramedullary nail 100. In one example, the grip 414 can have a generally cylindrical shape that extends along the select transverse direction T.

The first end portion 402 can include a coupler 408 that is configured to couple the handle 400 to the intramedullary nail 100. In at least some embodiments, the coupler 408 can be configured to couple the handle 400 to the intramedullary nail 100 such that the handle 400 and intramedullary nail 100 are rotationally fixed relative to one another. The first end portion 402 can define a cannulation 410 that extends through the first end portion 402 along the distal direction D. The cannulation 410 can be configured (e.g., sized and shaped) so as to receive a rod, such as a reaming rod, therein as the handle 400 guides the intramedullary nail 100 along the rod into the medullary canal of the bone. The cannulation 410 can be configured such that it is aligned with a cannulation of the intramedullary nail 100 when the handle 400 is coupled to the intramedullary nail 100. The cannulation 410 can extend through the coupler 408.

The handle 400 has a receptacle 412 that is configured to receive at least a portion of the strike instrument 500 so as to couple the strike instrument 500 to the handle 400. In one example, the receptacle 412 can be disposed at the first end portion 402 of the handle 400. For example, the receptacle 412 can be disposed between the coupler 408 and the grip 414 with respect to the select transverse direction T, although alternative locations are contemplated. The receptacle 412 can define a locking hole 416 that extends into the upper end 401 towards the lower end 403 along the distal direction D along a receptacle axis $A_R$. The locking hole 416 can be configured to receive a portion of the strike instrument, such as the abutment 508 and at least a portion of the shaft 506 of the strike instrument 500.

The locking hole 416 can include a proximal portion 416a, and a distal portion 416b that is offset from the proximal portion 416a along the distal direction D. The proximal portion 416a can have a length $l_1$ along a first transverse direction $T_1$ that is transverse to the receptacle axis $A_R$, and a width $w_1$ along a second transverse direction $T_2$ that is perpendicular to the first transverse direction $T_1$. The length $l_1$ of the proximal portion 416a can be greater than the width $w_1$ of the proximal portion 416b. Thus, the proximal portion 416a can be elongate along the first transverse direction $T_1$. The distal portion 416b can have a width $w_2$ along the second transverse direction $T_2$ that is greater than the width $w_1$ of the proximal portion 416a. The locking hole 416 can have an inner surface 418 that defines a shoulder of the locking hole 416 that adjoins the proximal portion 416a to the distal portion 416b. The inner surface 418 can face towards the distal direction D.

Figure 15:
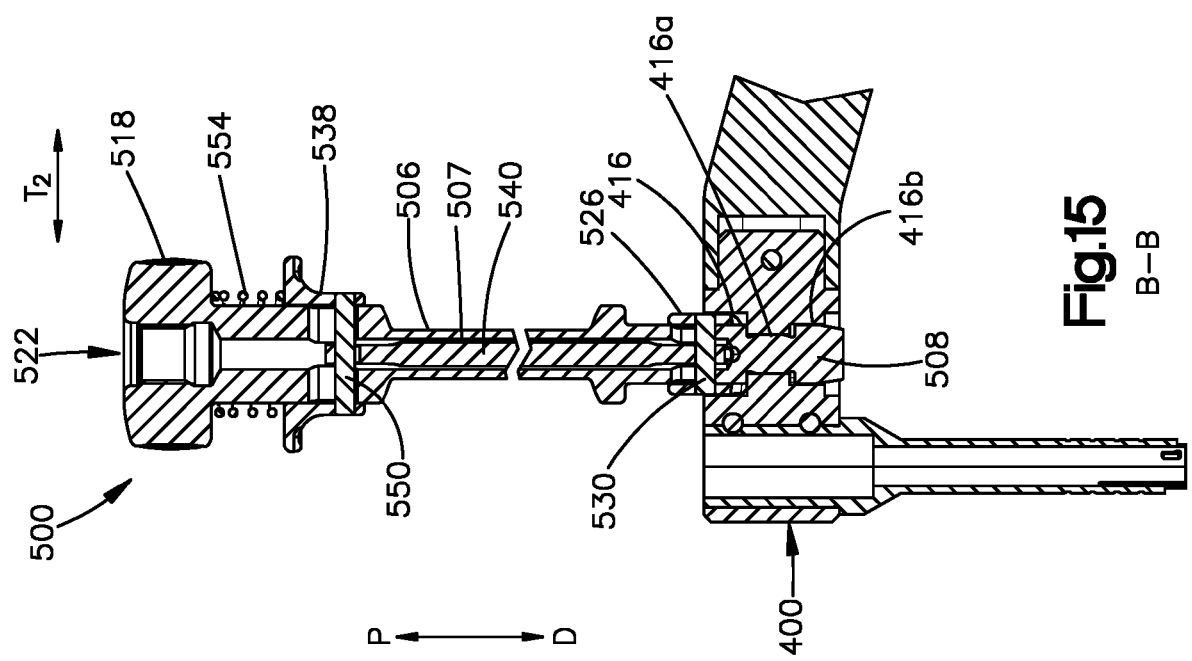
FIG. 15 shows a cross-sectional view of the system of FIGS. 9 and 10 taken along line B-B, with the strike instrument in a second rotational orientation.

The locking hole 416 can be sized and shaped to receive the abutment 508 through the proximal portion 416a of the locking hole 416 and into the distal portion 416b of the locking hole 416 when the abutment 508 is in the first rotational orientation relative to the insertion handle 400 (as shown in FIG. 14). For example, the length $l_1$ and width $w_1$ of the proximal portion 416a of the locking hole 416 can be greater than the length l and width w of the abutment 508, respectively. The locking hole 416 can be sized and shaped to lock the abutment 508 within the distal portion 416b when the abutment 508 is in the second rotational orientation relative to the insertion handle 400 (as shown in FIG. 15) so as to fix the strike instrument 500 to the insertion handle 400 with respect to translation along the proximal and distal directions P and D. For example, the width $w_1$ of the proximal portion 416a of the locking hole 416 can be less than the length l of the abutment 508, and the width $w_2$ of the distal portion 416b of the locking hole 416 can be greater than the length l of the abutment 508. When the abutment 508 is in the second rotational orientation relative to the insertion handle 400 (as shown in FIG. 15), the abutment 508 can abut the inner surface 418 of the insertion handle 400 so as to prevent the abutment 508, and consequently the strike instrument 500, from being moved relative to the insertion handle 400 along the proximal direction P.

The receptacle 412 can define at least one protrusion 425 that is configured to be received by at least one recess 525 of the strike instrument 500. In one example, the at least one protrusion 425 protrudes into the locking hole 410 of the insertion handle 400. In some embodiments, the at least one protrusion 425 can comprise first and second protrusion 425. The first and second protrusions 425 can be disposed on opposed sides of the receptacle axis $A_R$. For example, the first and second protrusions 425 can extend towards one another. It will be understood that the at least one protrusion can be positioned on the insertion handle in a different manner. The at least one protrusion 425 is configured to be receive by the at least one recess 525 of the lock 510 when the strike instrument 500 is in the second rotational orientation relative to the insertion handle 400 so as to rotationally fix the strike instrument 500 to the insertion handle 400. When the at least one recess 525 receives the at least one protrusion 425, inner walls of the lock 510 that define the at least one recess 525 interfere with the protrusion 425 so as to prevent the lock 510, and hence the strike instrument 3500, from being rotated about the shaft axis $A_S$ relative to the insertion handle 400.

The locking body 526 can include at least one ramped surface 527 (see FIG. 13) adjacent to the at least one recess 525. The at least one ramped surface 527 can be ramped towards the distal direction D as it extends towards the at least one recess 525. The at least one ramped surface 527 can extend about a portion of the sleeve 526 towards the at least one recess 525 along one of a clockwise and a counter clockwise direction. The at least one ramped surface 527 can be configured to ride along the at least one protrusion 425 of the insertion handle 400 as the strike instrument 500 is rotated from the first orientation to the second orientation, thereby causing the lock 510 to retract along the proximal direction P. Retraction of the lock 510 in the proximal direction P can compress at least one of the spring 554 and spring 534. When the at least one protrusion 425 is aligned with the at least one recess 525, the biasing force of the lock 510 biases the locking body 526, and hence the at least one recess 525, in the distal direction D to receive the at least one protrusion 425, thereby rotationally fixing the strike instrument 500 to the insertion handle 200.

Figure 19:
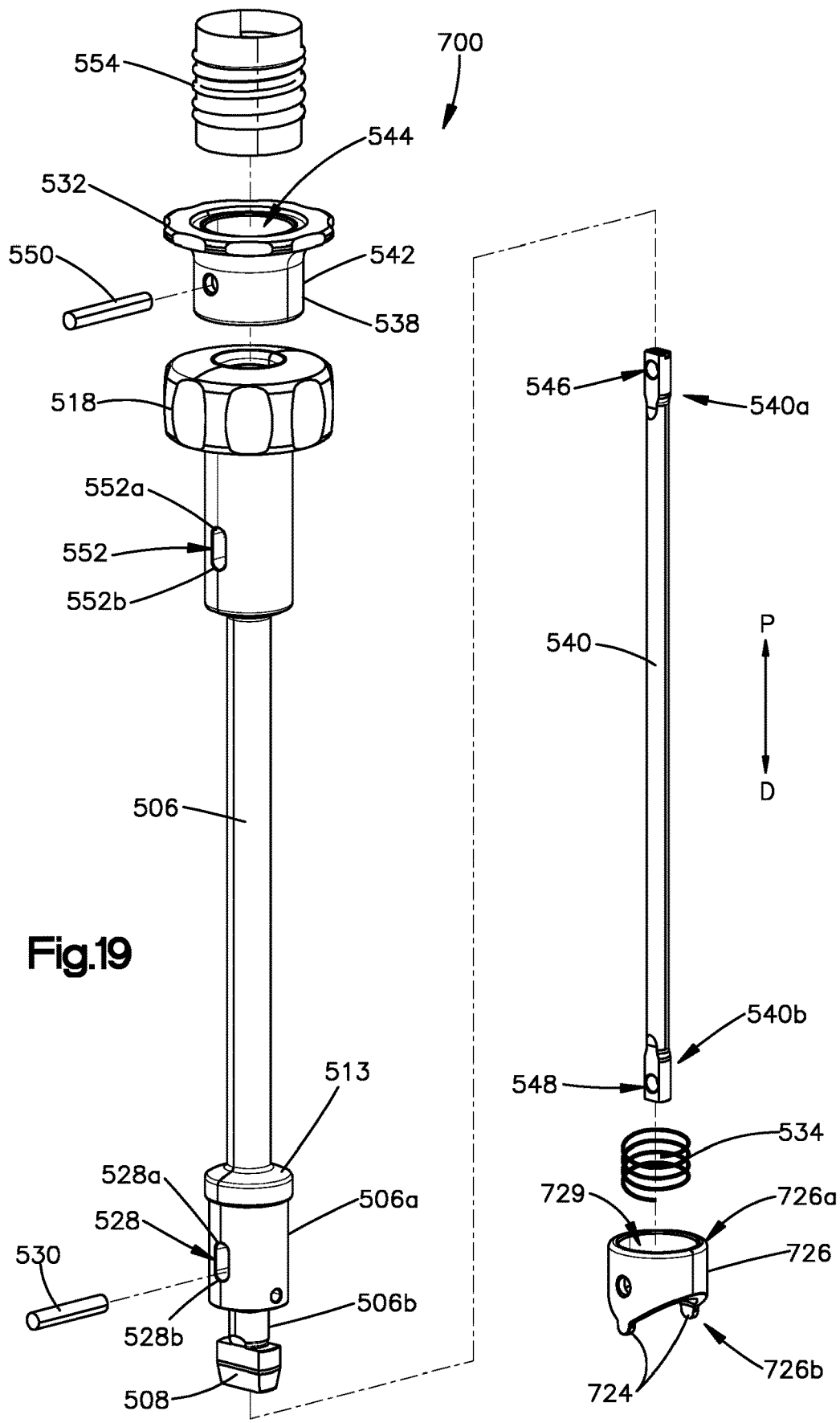
FIG. 19 shows an exploded perspective view of the strike instrument of FIGS. 17 and 18 according to one embodiment.
Figure 22:
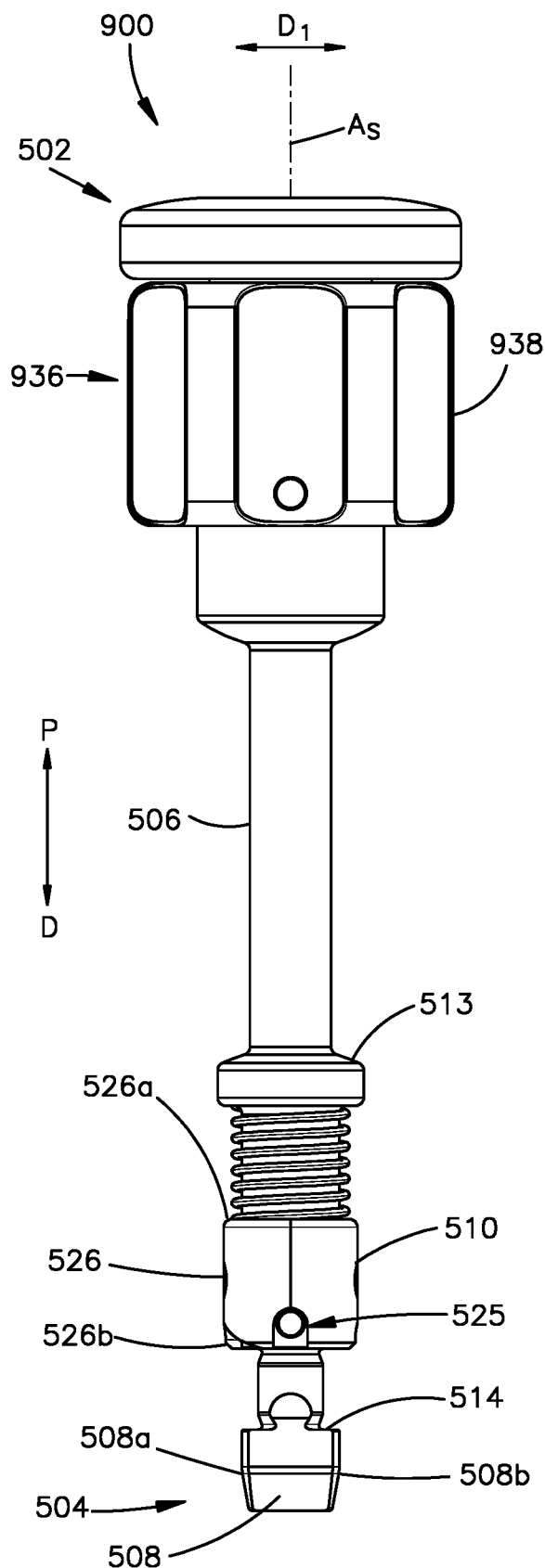
FIG. 22 shows a front elevation view of the strike instrument of FIGS. 20 and 21 according to one embodiment.
Figure 23:
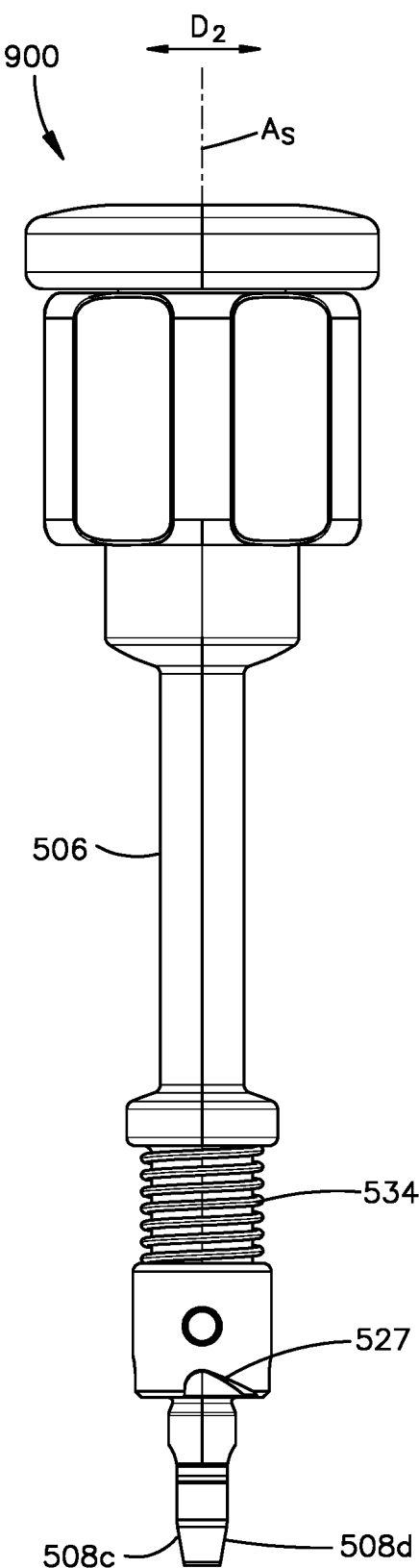
FIG. 23 shows a side elevation view of the strike instrument of FIG. 22.
Figure 24:
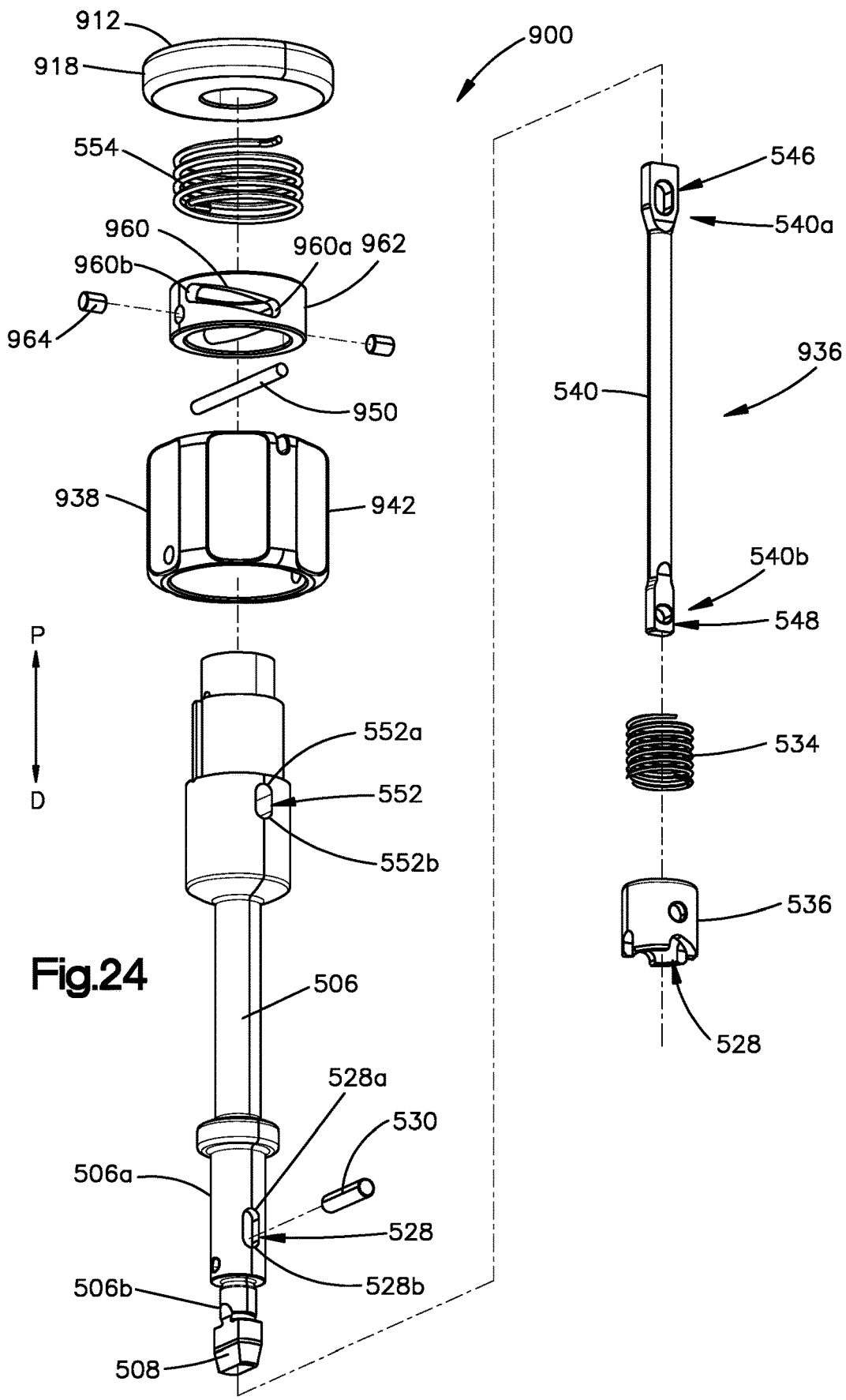
FIG. 24 shows an exploded perspective view of the strike instrument of FIG. 22.
Figure 27:
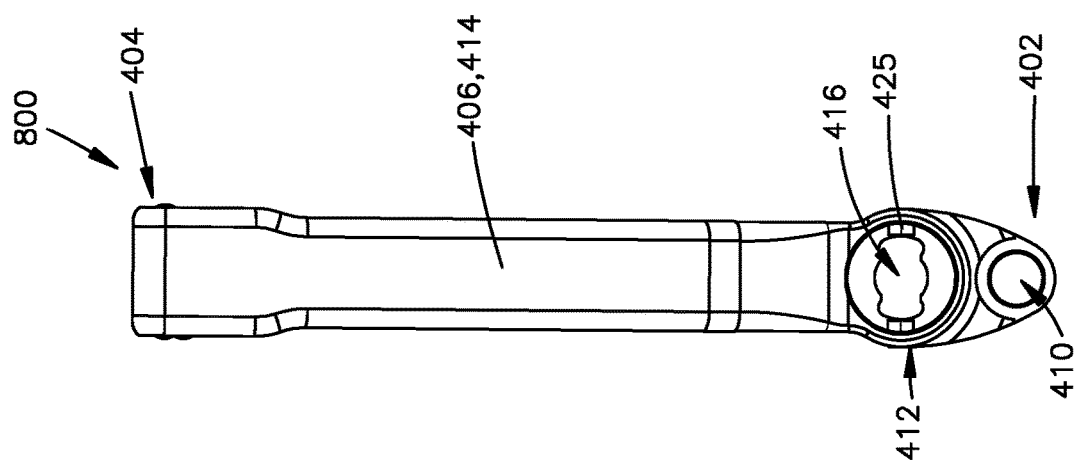
FIG. 27 shows a top plan view of the insertion handle of FIGS. 20 and 21 according to one embodiment.
Figure 26:
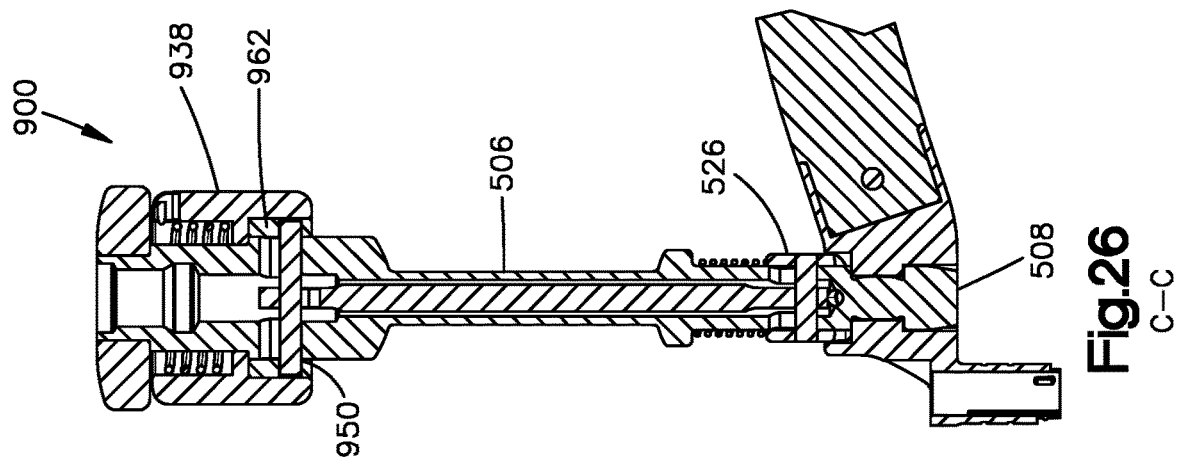
FIG. 26 shows a cross-sectional view of the system of FIGS. 20 and 21 taken along line C-C, with the strike instrument in a second rotational orientation.
Figure 25:
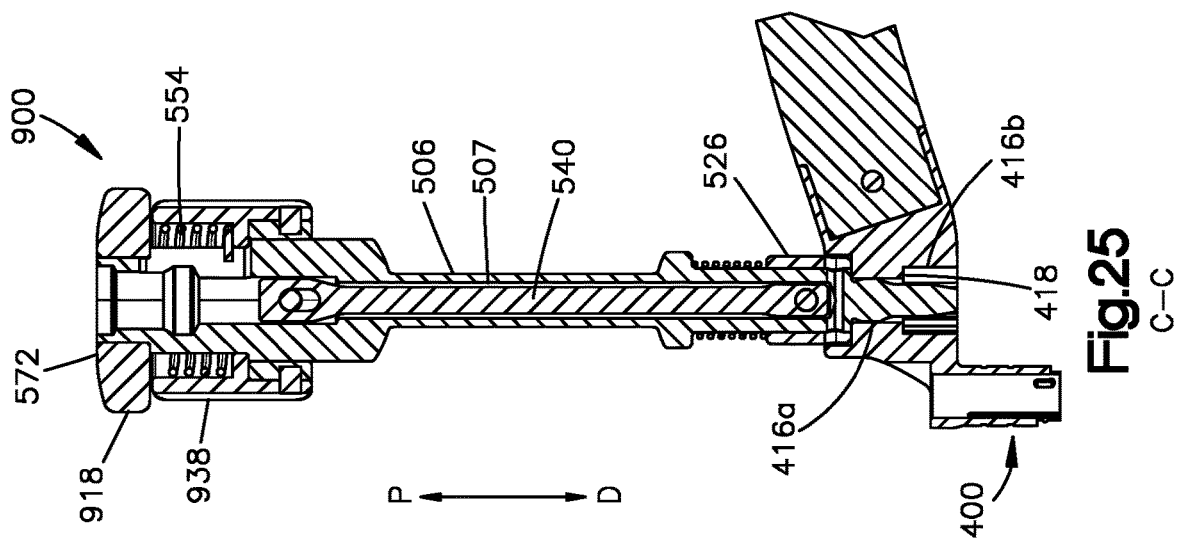
FIG. 25 shows a cross-sectional view of the system of FIGS. 20 and 21 taken along line C-C, with the strike instrument in a first rotational orientation.

Turning briefly to FIGS. 17 to 19, an embodiment is shown that is similar to the embodiment of FIGS. 9 to 16, except that (i) the lock 710 implements at least one protrusion 724 and (ii) the insertion handle 600 implements at least one recess 620. Note that features of FIGS. 17 to 19 that are similar to those of FIGS. 9 to 16 are labeled with like reference numerals. The at least one protrusion 724 can be implemented in a manner similar to the at least one protrusion 324 of FIGS. 1 to 8. The lock 710 can include the at least one protrusion 724 such that the at least one protrusion 724 is configured to engage at least one recess 620 of the handle 600 so as to prevent the shaft 506, and hence the abutment 508, from being rotated from the second rotational orientation to the first rotational orientation when the abutment 508 is received in the locking hole 616 of the handle 600. The at least one protrusion 724 can include a pair of protrusions 724 that are offset from one another. In one example, the protrusions 724 can be opposite one another on opposed sides of the shaft axis $A_S$.

The lock 710 can include a locking body 726 that includes the at least one protrusion 724. In one example, as shown, the locking body 726 can be a sleeve, although it will be understood that the locking body 726 can have any other suitable shape. The locking body 726 can have a proximal end 726a and a distal end 726b. The locking body 726 can define a channel 729 therethrough that extends from the proximal end 726a to the distal end 726b. The channel 729 can be configured to receive the shaft 506 therethrough such that the shaft 506 extends out of the proximal end 726a and the distal end 726b. The at least one protrusion 724 can extend from the distal end 726b along the distal direction D.

With continued reference to FIGS. 17 and 18, the at least one recess 620 can be implemented in a manner similar to the at least one recess 220 of FIGS. 1 to 8. The receptacle 612 can define the at least one recess 620 such that the at least one recess 620 extends into an upper surface of the insertion handle 600. In some embodiments, the at least one recess 620 can comprise first and second recesses 620. The first and second recesses 620 can be disposed on opposed sides of the locking hole 616. The at least one recess 620 is configured to receive at least one protrusion 724 of the lock 710 when the strike instrument 700 is in the second rotational orientation relative to the insertion handle 600 so as to rotationally fix the strike instrument 700 to the insertion handle 600. When the at least one recess 620 receives the at least one protrusion 724, inner walls of the insertion handle 600 that define the at least one recess 620 interfere with the protrusion 724 so as to prevent the lock 710, and hence the strike instrument 700, from being rotated about the shaft axis $A_S$ relative to the insertion handle 600.

The insertion handle 600 can include at least one ramped surface 622 adjacent to the at least one recess 620. The at least one ramped surface 622 can be ramped towards the proximal direction P as it extends towards the at least one recess 620. The at least one ramped surface 622 can extend about a portion of the locking hole 616 towards the at least one recess along one of a clockwise and a counter clockwise direction. The at least one ramped surface 622 can be configured to guide the at least one protrusion 724 of the lock 710 to ride up the ramped surface 622 as the strike instrument 700 is rotated from the first orientation to the second orientation, thereby causing the lock 710 to retract along the proximal direction P. Retraction of the lock 710 in the proximal direction P can compress the spring 534. When the at least one protrusion 724 is aligned with the at least one recess 620, the biasing force of the lock 710 biases the at least one protrusion 724 in the distal direction D into the at least one recess 620, thereby rotationally fixing the strike instrument 700 to the insertion handle 600.

In operation, a method can comprise a step of orienting the abutment 508 of the strike instrument (500, 700) in a first rotational orientation so as to align the abutment 508 with the locking hole 416 of the insertion handle (400, 600). The method can comprise a step of moving the strike instrument (500, 700) along the distal direction D so as to insert the abutment 508 through the proximal portion 416a of the locking hole 416 and into the distal portion 416b of the locking hole 416. The method can comprise a step of rotating the strike instrument (500, 700) from the first orientation to the second rotational orientation. The rotating step can comprise rotating the shaft 506 so as to cause the abutment 508 to rotate such that the abutment 508 engages an inner surface 418 of the locking hole 416, thereby preventing the strike instrument (500, 700) from being removed from the insertion handle (400, 600) along the proximal direction P. The method can comprise a step of locking the strike instrument (500, 700) in the second rotational orientation relative to the insertion handle (400, 600). The locking step can comprise a step of rotating the lock (510, 710) so as to cause at least one of a recess 525 and a protrusion 724 of the lock (510, 710) to engage another of at least one of a protrusion 425 and a recess 620 of the insertion handle (400, 600), thereby preventing the lock (510, 710) from being rotated relative to the insertion handle (400, 600). The step of rotating the lock (510, 710) can occur concurrently with the step of rotating the abutment 508. Thus, rotating the shaft 506 can resultingly rotate the abutment 508 and the lock (510, 710). The method can comprise a step of impacting the strike surface 512 and/or 513 of the strike instrument with a tool so as to drive the intramedullary nail 100 into the medullary canal.

To remove the strike instrument (500, 700), the method can comprise a step of translating the locking body 526 of the lock (510, 710) along the proximal direction P so as to disengage the at least one the recess 525 and the protrusion 724 of the lock (510, 710) from the at least one of the protrusion 425 and the recess 620 of the insertion handle (400, 600). The step of translating the locking body 526 can comprise a step of translating the handle 538 of the actuator 536 of the strike instrument (500, 700) along the proximal direction P, so as to cause the actuator shaft 540, and consequently, the locking body 536, to translate along the proximal direction from the locked position to the unlocked position. The method can comprise a step of rotating the strike instrument (500, 700) from the second rotational orientation to the first rotational orientation such that the interference between the abutment 508 and the inner surface 418 of the insertion handle (400, 600) is removed. The method can comprise a step of translating the strike instrument (500, 700) along the proximal direction P so as to remove the abutment 508 from the locking hole 416 of the insertion handle (400, 600).

Turning now to FIGS. 20 to 24, an embodiment is shown that can be implemented in a manner similar to that of FIGS. 9 to 16, except that the lock 910 has an actuator 936 that is implemented in an alternative manner. The strike instrument 900 has a shaft 506, an abutment 508, a locking body 526, a spring 534, a strike surface 513, and an actuator shaft 540 that are implemented as described above in relation to FIGS. 9 to 16. However, the actuator 936 is configured to rotate about the shaft 506 so as to cause the locking body 526 to move between the locked position and the unlocked position. The actuator 936 can comprise a handle 938 and the actuator shaft 540 that couples the handle 938 to the locking body 526. The actuator 936 can be configured such that rotation of the handle 938 about the shaft axis $A_S$ about a first rotational direction causes the actuator shaft 540 to translate along the proximal direction P, which in turn causes the locking body 526 to move along the proximal direction P from the locked position to the unlocked position. The actuator 936 can be configured such that rotation of the handle 938 about the shaft axis $A_S$ along a second rotational direction, opposite the first rotational direction, causes the actuator shaft 540 to translate along the distal direction D, which in turn causes the locking body 526 to move along the distal direction D from the unlocked position to the locked position.

The handle 938 can include a tubular body 942, although it will be understood that the handle 938 can have any other suitable shape. The handle 938 can define a cannulation 944 that is configured to receive the shaft 506. In at least some embodiments, the shaft 506 can extend through the handle 938 so as to extend out of opposed ends of the handle 938. The actuator 936 can include a fastener that couples the handle 938 to the shaft 506 such that the handle 938 is rotatable about the shaft 506.

The fastener can include a pin 950 that extends radially from, and is positionally fixed to, one of the shaft 506 and the handle 938. The pin 950 can be received through the fastener 546 of the actuator shaft 540 and into a slot 552 of another one of the shaft 506 and the handle 938. The slot 552 can be elongate along the proximal and distal directions P and D. The pin 950 can be configured to translate in the slot 552 along the proximal and distal directions P and D. In the embodiment of FIGS. 20 to 24, the shaft 506 defines the slot 552, and the pin 950 extends radially outward from the shaft 506, and is coupled to the handle 938. The pin 950 and slot 552 are configured such that, when the pin 950 is disposed in the slot 552, the pin 950 can translate within the slot 552 along the proximal and distal directions P and D. Thus, the actuator 936 is configured such that, when the handle 938 is rotated in the first rotational direction about the shaft axis $A_S$, the pin 950 translates along the proximal direction P, thereby causing the actuator shaft 540, and consequently the locking body 526, to translate along the proximal direction P. Conversely, when the handle 938 is rotated in the second rotational direction about the shaft axis $A_S$, the pin 950 translates along the distal direction D, thereby causing the actuator shaft 540, and consequently the locking body 526, to translate along the distal direction D.

The actuator 936 can define an angled slot 960 that is configured to receive the pin 950, and to translate the pin 950 along the proximal and distal directions P and D when the angled slot 960 is rotated about the shaft axis $A_S$. The angled slot 960 can have a first end 960a and a second end 960b that are offset from one another circumferentially about the shaft axis $A_S$. The angled slot 960 can be elongate from the first end 960a to the second end 960b. The second end 960b can be offset from the first end 960a with respect to the proximal direction P. Thus, the angled slot 960 can be angled towards the proximal direction P as it extends from the first end 960a to the second end 960b. The actuator 936 can be configured such that, when the handle 938 is rotated in the first rotational direction, the pin 950 rides along the angled slot 960 so as to translate in the proximal direction P. The actuator 936 can be configured such that, when the handle 938 is rotated in the second rotational direction, the pin 950 rides along the angled slot 960 so as to translate in the distal direction D. The angled slot 960 can be defined at an inner surface of the handle 938. Alternatively, the strike instrument 900 can include a collar 962 that defines the angled slot 960. The collar 962 can be rotationally fixed to the handle 938. For example, the strike instrument 900 can include at least one fastener 964, such as at least one pin, that fixedly couples the collar 962 to the handle 938. The collar 962 can be received in the cannulation 944 of the handle 938. The shaft 506 can be received in a cannulation of the collar 962.

The locking body 526 can be biased in the distal direction D towards the locked position. In other words, a biasing force can be applied to the locking body 526 to cause the locking body 526 to be biased in the distal direction D. For example, the lock 910 can include a spring 534 that biases the locking body 526 towards the locked position as described above. Additionally, or alternatively, the actuator 936 can comprise a spring 954 that biases the actuator 936 to rotate towards the locked position. The spring 954 can be a coil spring, such as a compression spring, an elastomeric material, or any other suitable spring that can bias the handle 938 to rotate towards the locked position. In one example, one end of the spring 954 can engage the knob 918 and the other end of the spring 954 can engage the handle 938.

The strike surface 912 can be disposed at the proximal end 502 of the strike instrument 900. In one example, the strike instrument 900 can include the knob 918 that defines the strike surface 912. The knob 918 can be disposed at the proximal end 502 of the strike instrument 900. The knob 918 can be rotationally fixed to the shaft 506. Thus, the strike instrument 900 can be configured such that rotation of the knob 918 causes a corresponding rotation of the shaft 506. The strike surface 912 can define a proximal-most surface of the strike instrument 900. The knob 918 can have a cross-sectional dimension along a select transverse direction $T_s$ that is greater than a cross-sectional dimension of the shaft 506 along the select transverse direction $T_s$. The select transverse direction $T_s$ can be perpendicular to the distal direction D. The knob 918 can define a grip that is configured to be grasped by a medical professional so as to rotate the shaft 506 between the first rotational orientation and the second rotational orientation.

In operation, and with reference to FIGS. 20, 21, 25, and 26, a method can comprise a step of orienting the abutment 508 of the strike instrument 900 in a first rotational orientation so as to align the abutment 508 with the locking hole 416 of the insertion handle 800. The method can comprise a step of moving the strike instrument 900 along the distal direction D so as to insert the abutment 508 through the proximal portion 416a of the locking hole 416 and into the distal portion 416b of the locking hole 416. The method can comprise a step of rotating the strike instrument 900 from the first orientation to the second rotational orientation. The rotating step can comprise rotating the shaft 506 so as to cause the abutment 508 to rotate such that the abutment 508 engages an inner surface 418 of the locking hole 416, thereby preventing the strike instrument 900 from being removed from the insertion handle 800 along the proximal direction P. The method can comprise a step of locking the strike instrument 900 in the second rotational orientation relative to the insertion handle 800. The locking step can comprise a step of rotating the lock 910 so as to cause at least one of a recess 525 and a protrusion 724 of the lock 910 to engage another of at least one of a protrusion 425 and a recess 620 of the insertion handle 800, thereby preventing the lock 910 from being rotated relative to the insertion handle 800. The step of rotating the lock 910 can occur concurrently with the step of rotating the abutment 508. Thus, rotating the shaft 506 can resultingly rotate the abutment 508 and the lock 910. The method can comprise a step of impacting the strike surface 912 and/or 913 of the strike instrument with a tool so as to drive the intramedullary nail 100 into the medullary canal.

To remove the strike instrument 900, the method can comprise a step of translating the locking body 526 of the lock 910 along the proximal direction P so as to disengage the at least one the recess 525 and the protrusion 724 of the lock 910 from the at least one of the protrusion 425 and the recess 620 of the insertion handle 800. The step of translating the locking body 526 can comprise a step of rotating the handle 938 of the actuator 936 of the strike instrument 900 about the shaft axis $A_S$, so as to cause the actuator shaft 540, and consequently, the locking body 526, to translate along the proximal direction P from the locked position to the unlocked position. The method can comprise a step of rotating the strike instrument 900 from the second rotational orientation to the first rotational orientation such that the interference between the abutment 508 and the inner surface 418 of the insertion handle 800 is removed. The method can comprise a step of translating the strike instrument 900 along the proximal direction P so as to remove the abutment 508 from the locking hole 416 of the insertion handle 800.

Figure 28:
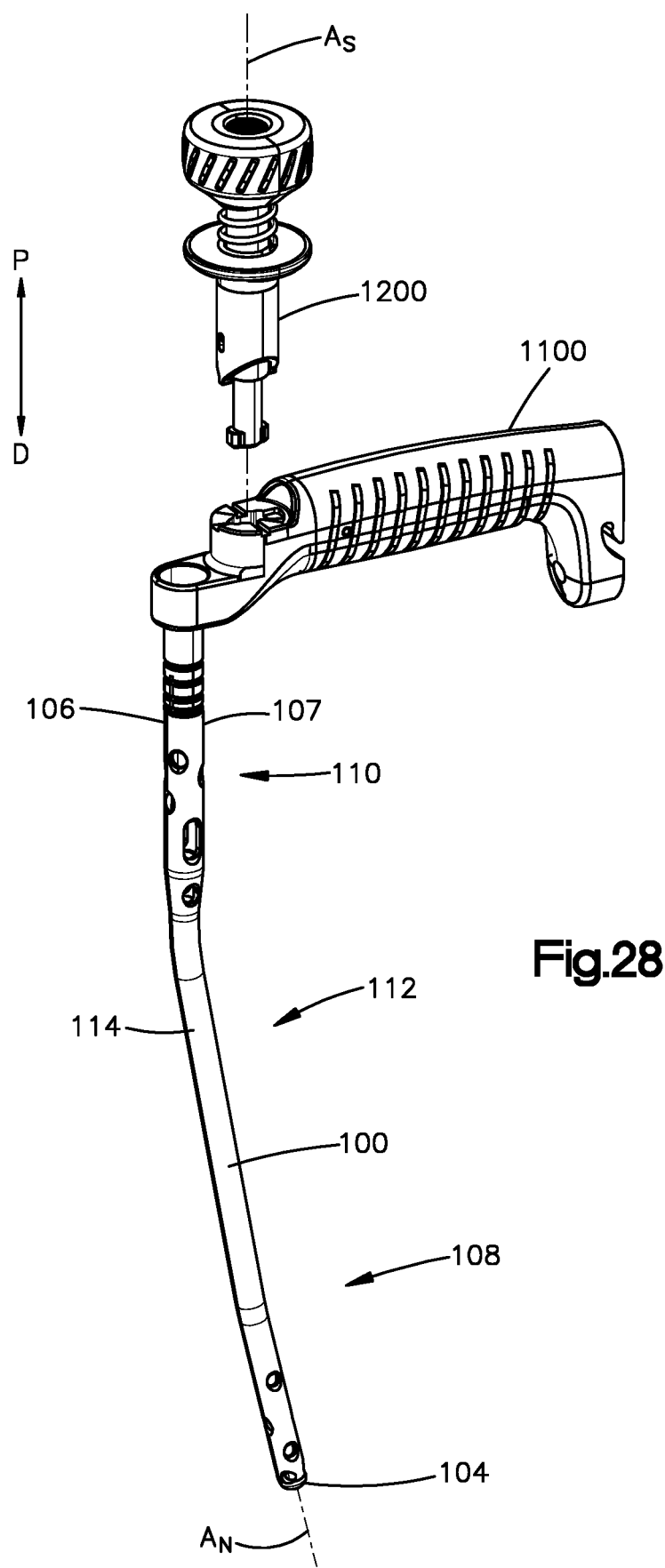
FIG. 28 shows a perspective view of a system according to one embodiment having an intramedullary nail, an insertion handle, and a strike instrument, with the strike instrument spaced from the insertion handle.

Referring briefly to FIG. 28, a system is shown that has an intramedullary nail 100, an insertion handle 1100, and a strike instrument 1200. The insertion handle 1100 can be implemented in a manner that is similar to any of the insertion handles described above. Similarly, the strike instrument 1200 can be implemented in a manner that is similar to any of the strike instruments described above. The intramedullary nail 100 has a distal end 104 and a proximal end 106 that are offset from one another. The distal end 104 can be considered to be an insertion end or leading end, and can define a first terminal or outermost end of the intramedullary nail 100. The proximal end 106 can be considered to be a trailing end and can define a second terminal or outermost end of the intramedullary nail 100. The proximal end 106 of the intramedullary nail 100 can include a coupler 107 configured to couple intramedullary nail 100 to the handle 200. In at least some examples, the coupler 107 can rotatably fix the handle 200 and intramedullary nail 100 relative to one another with respect to rotation about the nail axis AN. The coupler 107 can be configured to couple to a corresponding coupler (e.g., 208 in FIG. 1, 408 in FIGS. 9, 18, and 21) of the insertion handle 1100.

The intramedullary nail 100 is elongate from the proximal end 106 to the distal end 104. For instance, the intramedullary nail 100 is substantially elongate along a central pathway that extends from the proximal end 106 to the distal end 104. In at least some embodiments, the central pathway can be defined by a central axis $A_N$ of the intramedullary nail 100 that extends from the proximal end 106 to the distal end 104. It will be appreciated that the central pathway or central axis $A_N$ of the intramedullary nail 100 can be straight or curved. Thus, the intramedullary nail 100 can be straight or curved as it extends along the central pathway or central axis $A_N$ from the proximal end 106 to the distal end 104. The intramedullary nail 100 can be inserted into a medullary canal of a long bone such that the central pathway or central axis $A_N$ extends along the length of the medullary canal.

The intramedullary nail 100 has a leading or distal body portion 108 and a proximal body portion 110 that are offset from one another. The intramedullary nail 100 also has an intermediate body portion 112 between the distal body portion 108 and the proximal body portion 110. The distal body portion 108 can extend from the distal end 104 of the intramedullary nail 100 towards the proximal end 106 along the proximal direction P, which can also be referred to as a trailing direction. Further, the proximal body portion 110 can extend from the proximal end 106 towards the distal end 104 along the distal direction D, which can also be referred to as an insertion direction. For example, the distal body portion 108 can extend from the distal end 104 to the intermediate body portion 112, and the proximal body portion 110 can extend from the proximal end 106 to the intermediate body portion 112. It will be understood that the distal direction D extends from the proximal end 106 towards the distal end 104, and the proximal direction P extends in a direction opposite the distal direction D (i.e., from the distal end 104 towards the proximal end 106).

The intramedullary nail 100 has an outer surface 114 that extends from the distal body portion 108 to the proximal body portion 110. For instance, the outer surface 114 can extend from the proximal end 106 to the distal end 104. The outer surface 114 can define an outer-most perimeter of the intramedullary nail 100. Further, the outer surface 114 can have any suitable cross-sectional shape as desired. For example, the outer surface 114 can be substantially circular in cross section along a plane that is substantially perpendicular to the central pathway or central axis AN. In some embodiments, the intramedullary nail 100 can have an inner surface opposite the outer surface 114. Thus, the intramedullary nail 100 includes a tubular wall between the inner surface and the outer surface 114. The inner surface can define a cannulation that extends into the proximal end 106 in the distal direction D. The cannulation can extend to the distal body portion 108. For example, the cannulation can extend through the distal end 104. Alternatively, the cannulation can terminate prior to the distal end 104 such as in the distal body portion 108 or the intermediate body portion 112. In at least some embodiments, the cannulation can be configured (e.g., sized and shaped) so as to receive a rod, such as a reaming rod, therein as the intramedullary nail 100 is guided along the rod into the medullary canal of the bone. The cannulation can extend along the central pathway or central axis $A_N$ of the intramedullary nail 100.

The intramedullary nail 100 defines a plurality of bone-anchor fixation holes 124. Each bone-anchor fixation hole 124 is configured to receive a bone anchor so as to attach the intramedullary nail 100 to a bone. The bone-anchor fixation holes 124 can include at least one proximal bone-anchor fixation hole 126 and at least one distal bone-anchor fixation hole 128. Each of the at least one proximal bone-anchor fixation hole 126 extends into the proximal body portion 110 of the intramedullary nail 100. Similarly, each of the at least one distal bone-anchor fixation hole 128 extends into the distal body portion 108 of the intramedullary nail 100.

Each bone-anchor fixation hole 124 is configured to receive a bone anchor that extends through the bone-anchor fixation hole 124 so as to attach the intramedullary nail 100 to a bone. In particular, each bone-anchor fixation hole 124 can extend into the outer surface 114 and at least partially, such as entirely, through the intramedullary nail 100. For instance, each bone-anchor fixation hole 124 can extend into the outer surface 114 on a first side of the intramedullary nail 100 and out of the outer surface 114 on a second side of the intramedullary nail 100, opposite the first side. As such, each bone-anchor fixation hole 124 can be considered to be a through hole, although embodiments of the disclosure are not limited to through holes. Each bone-anchor fixation hole 124 can be unthreaded or can include internal threading to receive external threading of a bone anchor.

Although there has been shown and described the certain embodiments of the present disclosure, it will be readily apparent to those skilled in the art that modifications may be made thereto which do not exceed the scope of the appended claims. The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein. Accordingly, those skilled in the art will realize that the invention is intended to encompass all modifications and alternative arrangements included within the spirit and scope of the invention, as set forth by the appended claims.

It should be noted that the illustrations and descriptions of the examples and embodiments shown in the figures are for exemplary purposes only, and should not be construed limiting the disclosure. One skilled in the art will appreciate that the present disclosure contemplates various embodiments. Additionally, it should be understood that the concepts described above with the above-described examples and embodiments may be employed alone or in combination with any of the other examples and embodiments described above. It should further be appreciated that the various alternative examples and embodiments described above with respect to one illustrated embodiment can apply to all examples and embodiments as described herein, unless otherwise indicated.

Unless explicitly stated otherwise, each numerical value and range should be interpreted as being approximate as if the word "about," "approximately," or "substantially" preceded the value or range. The terms "about," "approximately," and "substantially" can be understood as describing a range that is within 15 percent of a specified value unless otherwise stated.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

What is claimed:

1. A strike instrument configured to couple to an insertion handle of an intramedullary nail, the strike instrument comprising:
    a proximal end, and a distal end that is opposite the proximal end along a distal direction;
    a shaft that extends between the proximal end and the distal end along a shaft axis;
    an abutment that extends outward relative to the shaft along a first direction such that the abutment defines a length in the first direction that is greater than a cross-sectional dimension of the shaft in the first direction, the abutment being rotationally fixed to the shaft such that the shaft is configured to rotate the abutment between a first rotational orientation, wherein the abutment can be removed or inserted into the insertion handle, and a second rotational orientation, wherein the abutment is configured to form an interference with the insertion handle that prevents the abutment from being removed from the insertion handle;
    a strike surface that is translatably fixed to the shaft and configured to receive an impaction force from an impaction tool so as to transfer the impaction force from the strike instrument to the insertion handle when the strike instrument is coupled to the insertion handle; and
    a lock configured such that, when the abutment is received in the insertion handle and rotated relative to the insertion handle from the first rotational orientation to the second rotational orientation, the lock engages the insertion handle so as to prevent the abutment from rotating from the second rotational orientation to the first rotational orientation.

2. The strike instrument of claim 1, wherein the lock includes at least one of a protrusion and a recess that is configured to engage another of a recess and a protrusion of the insertion handle so as to prevent the abutment from rotating from the second rotational orientation to the first rotational orientation.

3. The strike instrument of claim 1, wherein the lock is a releasable lock that is configured to be released from engagement with the insertion handle so as to permit the abutment to rotate from the second rotational orientation to the first rotational orientation, thereby allowing the strike instrument to be removed from the insertion handle along a proximal direction, opposite the distal direction.

4. The strike instrument of claim 1, wherein the length is defined in a plane that is perpendicular to the shaft axis, and the abutment has a width in the plane that is less than the length.

5. The strike instrument of claim 1, wherein the abutment includes at least one engagement surface that is configured to engage an inner surface of the insertion handle so as to define the interference with the inner surface of the insertion handle when the abutment is received in the insertion handle and rotated in the second rotational orientation.

6. The strike instrument of claim 1, wherein the strike instrument includes a force transfer surface that is translatably fixed relative to the shaft and configured to engage the insertion handle so as to transfer the impaction force to the insertion handle.

7. The strike instrument of claim 2, wherein the lock includes a locking body that includes the at least one of the protrusion and the recess of the lock, wherein the locking body is configured to translate relative to the shaft along shaft axis between a locked position and an unlocked position, wherein the at least one of the protrusion and the recess of the lock projects further along the distal direction in the locked position than in the unlocked position.

8. The strike instrument of claim 7, wherein the locking body is rotationally fixed to the shaft such that rotation of the shaft causes a corresponding rotation of the locking body.

9. The strike instrument of claim 7, wherein the lock comprises a flange that extends outwardly from the locking body, the flange configured to be engaged by a medical professional and moved along a proximal direction, opposite the distal direction, so as to remove the at least one of the protrusion and the recess of the lock from the another of the recess and the protrusion of the insertion handle.

10. The strike instrument of claim 7, wherein the lock comprises an actuator that is configured to be actuated so as to move the locking body between the locked position and the unlocked position.

11. The strike instrument of claim 10, wherein the actuator comprises an actuator handle and an actuator shaft, the actuator shaft being coupled to the actuator handle and the locking body such that movement of the actuator handle causes the actuator shaft to move the locking body between the locked position and the unlocked position.

12. A system, comprising:
the strike instrument of claim 1; and
the insertion handle.

13. The system of claim 12, wherein the insertion handle defines a locking hole that is configured to receive the abutment, the abutment and the locking hole having a keyed relationship with one another.

14. The system of claim 12, wherein the strike instrument is configured to be rotated between the first rotational orientation and the second rotational orientation by rotating the abutment by 180 degrees or less.

15. The system of claim 12, wherein:
the locking hole includes a proximal portion, and a distal portion that is offset from the proximal portion along the distal direction; and
the locking hole is configured to receive the abutment through the proximal portion and into the distal portion when the abutment is in the first rotational orientation, and the locking hole is configured to lock the abutment within the distal portion when the abutment is in the second rotational orientation so as to prevent the abutment from being removed from the locking hole along the proximal direction.

16. A method of coupling a strike instrument to an insertion handle of an intramedullary nail, comprising steps of:
orienting an abutment of the strike instrument in a first rotational orientation so as to align the abutment with a locking hole of the insertion handle;
moving the strike instrument along a distal direction so as to insert the abutment into the locking hole;
rotating the abutment from the first rotational orientation to a second rotational orientation so as to cause the abutment to engage an inner surface of the locking hole, thereby preventing the strike instrument from being removed from the insertion handle along a proximal direction, opposite the distal direction; and
locking the strike instrument in the second rotational orientation relative to the insertion handle.

17. The method of claim 16, wherein:
the moving step comprises moving the abutment through a proximal portion of the locking hole and into a distal portion of the locking hole, the distal portion having a width that is greater than a width of the proximal portion so as to define the inner surface extending between the proximal portion and the distal portion;
the abutment extends outward relative to a shaft of the strike instrument so as to define an engagement surface; and
the rotating step comprises rotating the abutment within the distal portion of the locking hole such that the engagement surface of the abutment interferes with the inner surface.

18. The method of claim 16, wherein the locking step comprises rotating a lock of the strike instrument so as to cause at least one of a protrusion and a recess of the lock to engage another of a recess and a protrusion of the insertion handle, thereby preventing the strike instrument from being rotated relative to the insertion handle.

19. The method of claim 18, wherein the method comprises concurrently performing the rotating step and the locking step.

20. The method of claim 16, comprising steps of:
translating a locking body of the strike instrument along a proximal direction so as to unlock the strike instrument;
rotating the abutment from the second rotational direction to the first rotational direction; and
moving the strike instrument along the proximal direction so as to remove the strike instrument from the insertion handle.

* * * * *